United States Patent
Jung et al.

(10) Patent No.: US 10,016,249 B2
(45) Date of Patent: Jul. 10, 2018

(54) ACCESSING PREDICTIVE DATA

(75) Inventors: Edward K. Y. Jung, Bellevue, WA (US); Royce A. Levien, Lexington, MA (US); Robert W. Lord, Seattle, WA (US); Mark A. Malamud, Seattle, WA (US); John D. Rinaldo, Jr., Bellevue, WA (US); Lowell L Wood, Jr., Livermore, CA (US)

(73) Assignee: Gearbox LLC, Bellevue, WA (US)

( * ) Notice: Subject to any disclaimer, the term of this patent is extended or adjusted under 35 U.S.C. 154(b) by 1471 days.

(21) Appl. No.: 11/585,662

(22) Filed: Oct. 23, 2006

(65) Prior Publication Data

US 2007/0118164 A1 May 24, 2007

Related U.S. Application Data

(63) Continuation-in-part of application No. 11/222,031, filed on Sep. 8, 2005, now abandoned, and a continuation-in-part of application No. 11/241,868, filed on Sep. 30, 2005, now abandoned, and a continuation-in-part of application No. 11/262,499, filed on Oct. 28, 2005, now abandoned, and a continuation-in-part of application No. 11/286,133, filed on Nov. 23, 2005, now abandoned, and a continuation-in-part of application No. 11/314,730, filed on Dec. 21, 2005.

(51) Int. Cl.
| | | |
|---|---|---|
| G06F 3/00 | (2006.01) | |
| G06K 9/36 | (2006.01) | |
| H05G 1/28 | (2006.01) | |
| A61B 90/00 | (2016.01) | |
| G16H 40/63 | (2018.01) | |
| G16H 50/50 | (2018.01) | |
| G16H 50/70 | (2018.01) | |
| A61B 34/10 | (2016.01) | |
| G16H 15/00 | (2018.01) | |

(52) U.S. Cl.
CPC ............ *A61B 90/36* (2016.02); *G16H 40/63* (2018.01); *G16H 50/50* (2018.01); *G16H 50/70* (2018.01); *A61B 34/10* (2016.02); *G16H 15/00* (2018.01)

(58) Field of Classification Search
CPC ...... G06Q 50/22; G06Q 50/24; G06F 19/322; G06F 19/3406
USPC ........................................................ 705/2–3
See application file for complete search history.

(56) References Cited

U.S. PATENT DOCUMENTS

| | | |
|---|---|---|
| 5,505,623 A | 4/1996 | Chernack et al. |
| 5,953,704 A | 9/1999 | McIlroy et al. |
| 6,157,921 A | 12/2000 | Barnhill |
| 6,317,731 B1 | 11/2001 | Luciano |

(Continued)

OTHER PUBLICATIONS

U.S. Appl. No. 11/586,439, Jung et al.

(Continued)

*Primary Examiner* — Joy Chng

(57) ABSTRACT

An apparatus, device, methods, computer program product, and system are described that provide a graphical illustration of a first possible outcome of a use of a treatment parameter with respect to at least one body portion, the first possible outcome based on at least one dataset associated with at least one predictive basis, and apply a filter criteria to the at least one dataset to provide a modified graphical illustration of a second possible outcome of the use of the treatment parameter.

25 Claims, 19 Drawing Sheets

| | 306 Treatment Parameter Direct End Target | 308 Discriminated End Target | 310 Direct Intermediate Targets | 312 Discriminated Intermediate Targets | 314 Target-Related, Tissue Ancestry-Correlated Binding Site | 316 Target-Related, Tissue Ancestry-Correlated Binding Agent | 318 Treatment Agent Delivery Mechanism Relative to Target-Related, Tissue Ancestry-Correlated Binding Agent | 320 Treatment Agent |
|---|---|---|---|---|---|---|---|---|
| 502 | Lung Tissue | Non-Lung Tissue | Endothelial Tissue proximate to Lung Tissue | Endothelial Tissue proximate to Non-Lung Tissue | APP associated with Intermediate Target | I-labeled monoclonal APP Antibodies | Essentially Direct | Radio-immunotherapy via Low-Levels of radionuclides |
| 504 | Lung Tissue | Non-Lung Tissue | Endothelial Tissue proximate to Lung Tissue | Endothelial Tissue proximate to Non-Lung Tissue | APP associated with Intermediate Target | Binding Agent X | Essentially Direct | Treatment Agent X |
| 506 | Diseased Lung Tissue | Non-Diseased Lung Tissue | Endothelial Tissue proximate to Diseased Lung Tissue | Endothelial Tissue proximate to Non-Diseased Lung Tissue | 15 differentially expressed proteins associated with Endothelial Tissue | I-labeled monoclonal APP Antibodies generated for selected one(s) of the 15 proteins | Essentially Direct | Radio-immunotherapy via Low-Levels of radionuclides |

(56) References Cited

U.S. PATENT DOCUMENTS

| | | | |
|---|---|---|---|
| 6,450,956 B1 | 9/2002 | Rappaport et al. | |
| 6,615,209 B1 | 9/2003 | Gomes et al. | |
| 6,826,578 B2 | 11/2004 | Brackett et al. | |
| 6,904,434 B1 | 6/2005 | Wallach et al. | |
| 6,963,878 B2 | 11/2005 | Anson | |
| 7,581,191 B2* | 8/2009 | Rice | A61B 5/0059 |
| | | | 382/128 |
| 7,730,063 B2 | 6/2010 | Eder | |
| 8,163,896 B1 | 4/2012 | Bentwich | |
| 2002/0083075 A1 | 6/2002 | Brummel et al. | |
| 2002/0099273 A1 | 7/2002 | Bocionek et al. | |
| 2002/0099686 A1 | 7/2002 | Schwartz et al. | |
| 2002/0186818 A1* | 12/2002 | Arnaud | A61B 6/583 |
| | | | 378/165 |
| 2002/0188183 A1 | 12/2002 | Kusakabe et al. | |
| 2003/0016850 A1 | 1/2003 | Kaufman et al. | |
| 2003/0069758 A1 | 4/2003 | Anderson et al. | |
| 2003/0135087 A1 | 7/2003 | Hickle et al. | |
| 2003/0138432 A1 | 7/2003 | Glazier | |
| 2004/0009459 A1 | 1/2004 | Anderson et al. | |
| 2004/0039602 A1 | 2/2004 | Greenberg et al. | |
| 2004/0054358 A1 | 3/2004 | Cox et al. | |
| 2004/0068514 A1 | 4/2004 | Chundi et al. | |
| 2004/0133095 A1 | 7/2004 | Dunki-Jacobs et al. | |
| 2004/0215651 A1 | 10/2004 | Markowitz et al. | |
| 2004/0267574 A1 | 12/2004 | Stefanchik et al. | |
| 2005/0113297 A1 | 5/2005 | Francois et al. | |
| 2006/0024231 A1 | 2/2006 | Schnitzer et al. | |
| 2008/0120267 A1 | 5/2008 | Chen et al. | |

OTHER PUBLICATIONS

U.S. Appl. No. 11/586,349, Jung et al.
U.S. Appl. No. 11/585,784, Jung et al.
U.S. Appl. No. 11/540,927, Jung et al.
U.S. Appl. No. 11/516,689, Jung et al.
U.S. Appl. No. 11/503,501, Jung et al.
U.S. Appl. No. 11/478,295, Jung et al.
U.S. Appl. No. 11/471,289, Jung et al.
U.S. Appl. No. 11/362,545, Jung et al.
U.S. Appl. No. 11/347,804, Jung et al.
U.S. Appl. No. 11/343,965, Jung et al.
U.S. Appl. No. 11/314,730, Jung et al.
U.S. Appl. No. 11/311,906, Jung et al.
U.S. Appl. No. 11/286,133, Jung et al.
U.S. Appl. No. 11/262,499, Jung et al.
U.S. Appl. No. 11/241,868, Jung et al.
U.S. Appl. No. 11/222,031, Jung et al.
Aird et al.; "Vascular Bed-Specific Expression of an Endothelial Cell Gene Is Programmed by the Tissue Microenvironment"; The Journal of Cell Biology; Bearing a date of Sep. 8, 1997; pp. 1117-1124; vol. 138, No. 5; © The Rockefeller University Press.
Brody, Lawrence C.; "Treating Cancer by Targeting a Weakness," The New England Journal of Medicine; Bearing a date of Sep. 1, 2005, Aug. 31, 2005 and 2005; pp. 949-950; © Massachusetts Medical Society.
Bryant et al.; "Specific killing of BRCA2-deficient tumours with inhibitors of poly(ADP-ribose) polymerase," Nature; Bearing a date of Apr. 14, 2005 and 2005; vol. 434; pp. 917-921; Nature Publishing Group.
Cahalan et al.; "Real-time imaging of lymphocytes in vivo"; Current Opinion in Immunology; Bearing a date of 2003; pp. 372-377; vol. 15.
Carver et al.; "Caveolae: Mining Little Caves for New Cancer Targets"; Nature Reviews; Bearing dates of Aug. 2003 and 2003; pp. 571-581; vol. 3; Nature Publishing Group.
Condeelis et al.; "Intravital Imaging of Cell Movement in Tumours"; Nature Reviews; Bearing a date of Dec. 2003; pp. 921-930; vol. 3.

Contag et al.; "The writing is on the vessel wall"; Nature; Bearing dates of Jun. 10, 2004 and 2004; pp. 618-619; vol. 429; Nature Publishing Group.
"DrugTarget Portal™"; LifeSpan Biosciences; Bearing a date of 2005; printed on Sep. 12, 2005; pp. 1-2; located at: https://www.lsbio.com/products/expression/DrugTargetDB.aspx; LifeSpan, Inc.
Essler et al.; "Molecular specialization of breast vasculature: A breast-homing phage-displayed peptide binds to aminopeptidase P in breast vasculature"; bearing a date of Feb. 19, 2002; pp. 2252-2257; vol. 99; No. 4.
Farmer et al.; "Targeting the DNA repair defect in BRCA mutant cells as a therapeutic strategy," Bearing dates of Apr. 14, 2005 and 2005; Nature, vol. 434; pp. 913-917; © Nature Publishing Group.
Folkman, Judah; "Looking for a good endothelial address"; Cancer Cell; Bearing a date of Mar. 2002; pp. 113-115.
"Gene Family Localization Data"; LifeSpan Biosciences; Bearing a date of 2005; printed on Sep. 12, 2005; pp. 1-3; located at: https://www.lsbio.com/products/expression/familyspecific.aspx.
Hood et al.; "Tumor Regression by Targeted Gene Delivery to the Neovasculature"; Science; Bearing dates of Jun. 28, 2002 and Oct. 2002; pp. 2404-2407 and 1; vol. 296.
Hsu et al.; "Neural Systems Responding to Degrees of Uncertainty in Human Decision-Making"; Science; bearing a date of Dec. 9, 2005; pp. 1680-1683; vol. 310.
Hu et al.; "Targeting tissue factor on tumor vascular endothelial cells and tumor cells for immunotherapy in mouse models of prostatic cancer"; PNAS; Bearing dates of Aug. 9, 2001 and Oct. 9, 2001; vol. 98; No. 21.
Kaplan et al.; " VEGFR1-positive haematopoietic bone marrow progenitors initiate the pre-metastatic niche"; Nature; Bearing dates of Dec. 8, 2005 and 2005; vol. 438; pp. 820-827; © 2005 Nature Publishing Group.
"LifeSpan DrugTarget™"; Lifespan Biosciences; Bearing a date of 2005; printed on Sep. 12, 2005; pp. 1-2; located at: https://www.lsbio.com/products/expression/DrugTargetDB.aspx; LifeSpan, Inc.
"LifeSpan FlexModule Database™"; LifeSpan Biosciences; Bearing a date of 2005; printed on Sep. 12, 2005; pp. 1-2; located at: https://www.lsbio.com/Products/expression/flexmodule.aspx; LifeSpan, Inc.
M'Rini et al.; "A Novel Enodthelial L-Selectin Ligand Activity in Lymph Node Medulla That Is Regulated by $\alpha^1(1,3)$-Fucosyltransrerase-IV"; J. Exp. Med.; Bearing a date of Nov. 3, 2003; vol. 198, No. 9; © The Rockefeller University Press.
Madri et al.; "Capillary Endothelial Cell Cultures: Phenotypic Modulation by Matrix Components"; The Journal of Cell Biology; Bearing a date of Jul. 1983; pp. 153-165; vol. 97; © The Rockefeller University Press.
McIntosh et al.; "Targeting endothelium and its dynamic caveolae for tissue-specific transcytosis in vivo: A pathway to overcome cell barriers to drug and gene delivery"; PNAS; Bearing a date of Feb. 19, 2002; pp. 1996-2001; vol. 99; No. 4.
Oh et al.; "Immunoisolation of Caveolae with High Affinity Antibody Binding to the Oligomeric Caveolin Cage"; The Journal of Biological Chemistry; Bearing dates of Aug. 13, 1999, Aug. 31, 1998, and May 10, 1999; pp. 23144-23154; vol. 274, No. 33.
Oh et al.; "Subtractive Proteomic Mapping of the Endothelial Surface in Lung and Solid Tumors for Tissue-Specific Therapy"; Nature; Bearing dates of Jun. 10, 2004 and 2004; pp. 629-635; vol. 429; © 2004 Nature Publishing Group.
Pasqualini et al.; "Organ targeting in vivo using phage display peptide libraries"; Nature; Bearing a date of Mar. 28, 1996; pp. 364-366; vol. 380.
Pasqualini et al.; "Probing the structural and molecular diversity of tumor vasculature"; Trends in Molecular Medicine; Bearing dates of Dec. 2002 and 2002; pp. 563-571; vol. 8 No. 12; © 2002 Elsevier Science Ltd.
Perou et al.; "Molecular portraits of human breast tumours"; Nature; Bearing a date of Aug. 17, 2000; pp. 747-752; vol. 406; © 2000 Macmillan Magazines Ltd.
Rajotte et al.; "Molecular Heterogeneity of the Vascular Endothelium Revealed by in Vivo Phage Display"; J. Clin. Invest.;

(56) References Cited

OTHER PUBLICATIONS

Bearing dates of Feb. 6, 1998, May 21, 1998 and Jul. 1998; pp. 430-437; vol. 102, No. 2; © The American Society for Clinical Investigation, Inc.

Schnitzer et al.; "Separation of Caveolae from Associated Microdomains of GPI-Anchored Proteins"; Science; Bearing a date of Sep. 8, 1995; pp. 1435-1439; vol. 269.

"Tissue Specific Localization Data"; LifeSpan Biosciences; Bearing a date of 2005; printed Sep. 12, 2005; pp. 1-6; located at: https://www.lsbio.com/products/expression/tissuespecific.aspx; LifeSpan, Inc.

"3-D Computer Display Brings Precision to Burn Assessment"; ScienceDaily.com; Oct. 18, 1997; pp. 1-3.

Kay et al.; "Surgical planning for radical prostatectomies using three-dimensional visualization and a virtual reality display system"; bearing a date of 1995 [retrieved on Dec. 6, 2013]; pp. 119-125; vol. 2431; SPIE Digital Library; located at: http://spiedigitallibrary.org.

Robb et al.; "Computer-Aided Surgery Planning and Rehearsal at Mayo Clinic"; Jan. 1996; pp. 39-47; IEEE.

Balyasnikova et al.; "Epitope-specific antibody-induced cleavage of angiotensin-converting enzyme from the cell surface"; Biochemical Journal; Dec. 21, 2001; pp. 585-595; vol. 362.

Huang et al.; "Identification of ribosomal RNA genes in metagenomic fragments"; Bioinformatics; Mar. 17, 2009; pp. 1338-1340; vol. 25, No. 10.

Muzykantov, Vladimir R.; "Immunotargeting of drugs to the pulmonary vascular endothelium as a therapeutic strategy"; Pathophysiology; Mar. 3, 1998; pp. 15-33; vol. 5; Elsevier Science Ireland Ltd.

\* cited by examiner

FIG. 3

| | 304 Treatment Characteristics | | | | | | |
|---|---|---|---|---|---|---|---|
| | 306 Direct End Target | 308 Discriminated End Target | 310 Direct Intermediate Targets | 312 Discriminated Intermediate Targets | 314 Target-Related, Tissue Ancestry-Correlated Binding Site | 316 Target-Related, Tissue Ancestry-Correlated Binding Agent | 318 Treatment Agent Delivery Mechanism Relative to Target-Related, Tissue Ancestry-Correlated Binding Agent | 320 Treatment Agent |
| 302a Treatment Parameter | | | | | | | | |
| 302b Treatment Parameter | | | | | | | | |

FIG. 5

| 306 Treatment Parameter Direct End Target | 308 Discriminated End Target | 310 Direct Intermediate Targets | 312 Discriminated Intermediate Targets | 314 Target-Related, Tissue Ancestry-Correlated Binding Site | 316 Target-Related, Tissue Ancestry-Correlated Binding Agent | 318 Treatment Agent Delivery Mechanism Relative to Target-Related, Tissue Ancestry-Correlated Binding Agent | 320 Treatment Agent |
|---|---|---|---|---|---|---|---|
| Lung Tissue | Non-Lung Tissue | Endothelial Tissue proximate to Lung Tissue | Endothelial Tissue proximate to Non-Lung Tissue | APP associated with Intermediate Target | I-labeled monoclonal APP Antibodies | Essentially Direct | Radio-immunotherapy via Low-Levels of radionuclides |
| Lung Tissue | Non-Lung Tissue | Endothelial Tissue proximate to Lung Tissue | Endothelial Tissue proximate to Non-Lung Tissue | APP associated with Intermediate Target | Binding Agent X | Essentially Direct | Treatment Agent X |
| Diseased Lung Tissue | Non-Diseased Lung Tissue | Endothelial Tissue proximate to Diseased Lung Tissue | Endothelial Tissue proximate to Non-Diseased Lung Tissue | 15 differentially expressed proteins associated with Endothelial Tissue | I-labeled monoclonal APP Antibodies generated for selected one(s) of the 15 proteins | Essentially Direct | Radio-immunotherapy via Low-Levels of radionuclides |

502 → (row 1)
504 → (row 2)
506 → (row 3)

FIG. 6

| 306 Treatment Parameter Direct End Target | 308 Discriminated End Target | 310 Direct Intermediate Targets | 312 Discriminated Intermediate Targets | 314 Target-Related, Tissue Ancestry-Correlated Binding Site | 316 Target-Related, Tissue Ancestry-Correlated Binding Agent | 318 Treatment Agent Delivery Mechanism Relative to Target-Related, Tissue Ancestry-Correlated Binding Agent | 320 Treatment Agent and/or 402 Treatment Agent Precursor |
|---|---|---|---|---|---|---|---|
| Breast Tissue | Pancreas Tissue | Vascular Beds of Breast Tissue | Vascular Beds of Pancreas Tissue | APP of Vascular Bed of Breast Tissue | CPGPEGAGC peptide | Essentially Direct | Phages |
| Melanoma Tumors | Surrounding Non-tumor tissues | Endothelial Cells having Integrin avB3 | Endothelial Cells without Integrin avB3 | Integrin avB3 | AvB3 ligand | Cationic polymerized lipid-based nanoparticles | Coupled gene |

602 → (row 1)
604 → (row 2)

FIG. 7

| | 306 Treatment Parameter Direct End Target | 308 Discriminated End Target | 310 Direct Intermediate Targets | 312 Discriminated Intermediate Targets | 314 Target-Related, Tissue Ancestry-Correlated Binding Site | 316 Target-Related, Tissue Ancestry-Correlated Binding Agent | 318 Treatment Agent Delivery Mechanism Relative to Target-Related, Tissue Ancestry-Correlated Binding Agent | 320 Treatment Agent |
|---|---|---|---|---|---|---|---|---|
| 702 | Lung Tissue(s) | Tissues other than Lung | Endothelial Cell Caveolae Proximate to Lung | Endothelial Cell Caveolae Distal from Lung | Antigen to which monoclonal antibody TX3.833 binds | Monoclonal antibody TX3.833 | Essentially Direct via Endothelial Cell Caveolae | Gold |
| 704 | Prostrate Tumors in Mice | All other tissues | Tissue Factor(s) expressed by/on endothelial cells near tumor and by/on tumor itself | Tissue Factor in Other Locations | Tissue Factor | Factor VII, a ligand for tissue factor | Essentially Direct | Fc Effector Domain |
| 706 | Metastatic Niche(s) | Tissues other than Metastatic Niche(s) | Endothelial cells at Metastatic Niche(s) | Endothelial Cells at Other Locations | VEGFR1 | Antibody to VEGFR1 | Essentially Direct | Antibody to VEGFR1 |

ACCESSING PREDICTIVE DATA

CROSS-REFERENCE TO RELATED APPLICATIONS

The present application is related to, claims the earliest available effective filing date(s) from (e.g., claims earliest available priority dates for other than provisional patent applications; claims benefits under 35 USC § 119(e) for provisional patent applications), and incorporates by reference in its entirety all subject matter of the following listed application(s) (the "Related Applications") to the extent such subject matter is not inconsistent herewith; the present application also claims the earliest available effective filing date(s) from, and also incorporates by reference in its entirety all subject matter of any and all parent, grandparent, great-grandparent, etc. applications of the Related Application(s) to the extent such subject matter is not inconsistent herewith. The United States Patent Office (USPTO) has published a notice to the effect that the USPTO's computer programs require that patent applicants reference both a serial number and indicate whether an application is a continuation or continuation in part. Kunin, Benefit of Prior-Filed Application, USPTO Electronic Official Gazette, Mar. 18, 2003 at http://www.uspto.gov/web/offices/com/sol/og/2003/week11/patbene.htm. The present applicant entity has provided below a specific reference to the application(s) from which priority is being claimed as recited by statute. Applicant entity understands that the statute is unambiguous in its specific reference language and does not require either a serial number or any characterization such as "continuation" or "continuation-in-part." Notwithstanding the foregoing, applicant entity understands that the USPTO's computer programs have certain data entry requirements, and hence applicant entity is designating the present application as a continuation in part of its parent applications, but expressly points out that such designations are not to be construed in any way as any type of commentary and/or admission as to whether or not the present application contains any new matter in addition to the matter of its parent application(s).

RELATED APPLICATIONS

1. For purposes of the USPTO extra-statutory requirements, the present application constitutes a continuation in part of currently co-pending United States patent application entitled Data Techniques Related to Tissue Coding, naming Edward K. Y. Jung, Robert W. Lord, and Lowell L. Wood, Jr., as inventors, U.S. Ser. No. 11/222,031, filed Sep. 8, 2005.
2. For purposes of the USPTO extra-statutory requirements, the present application constitutes a continuation in part of currently co-pending United States patent application entitled Data Techniques Related to Tissue Coding, naming Edward K. Y. Jung, Robert W. Lord, and Lowell L. Wood, Jr., as inventors, U.S. Ser. No. 11/241,868, filed Sep. 30, 2005.
3. For purposes of the USPTO extra-statutory requirements, the present application constitutes a continuation in part of currently co-pending United States patent application entitled Accessing Data Related to Tissue Coding, naming Edward K. Y. Jung, Robert W. Lord, and Lowell L. Wood, Jr., as inventors, U.S. Ser. No. 11/262,499, filed Oct. 28, 2005.
4. For purposes of the USPTO extra-statutory requirements, the present application constitutes a continuation in part of currently co-pending United States patent application entitled Accessing Data Related to Tissue Coding, naming Edward K. Y. Jung, Robert W. Lord, and Lowell L. Wood, Jr., as inventors, U.S. Ser. No. 11/286,133, filed Nov. 23, 2005.
5. For purposes of the USPTO extra-statutory requirements, the present application constitutes a continuation in part of currently co-pending United States patent application entitled Accessing Predictive Data, naming Edward K.Y. Jung, Royce A. Levien, Robert W. Lord, Mark A. Malamud, John D. Rinaldo, and Lowell L. Wood, Jr., as inventors, U.S. Ser. No. 11/314,730, filed Dec. 21, 2005.

TECHNICAL FIELD

This description relates to data handling techniques.

SUMMARY

An embodiment provides a method. In one implementation, the method includes but is not limited to providing a graphical illustration of a first possible outcome of a use of a treatment parameter with respect to at least one body portion, the first possible outcome based on at least one dataset associated with at least one predictive basis and applying a filter criteria to the at least one dataset to provide a modified graphical illustration of a second possible outcome of the use of the treatment parameter. In addition to the foregoing, other method aspects are described in the claims, drawings, and text forming a part of the present disclosure.

An embodiment provides a computer program product. In one implementation, the computer program product includes but is not limited to a signal-bearing medium bearing at least one of one or more instructions for providing a graphical illustration of a first possible outcome of a use of a treatment parameter with respect to at least one body portion, the first possible outcome based on at least one dataset associated with at least one predictive basis, and the signal bearing medium bearing one or more instructions for applying a filter criteria to the at least one dataset to provide a modified graphical illustration of a second possible outcome of the use of the treatment parameter. In addition to the foregoing, other computer program product aspects are described in the claims, drawings, and text forming a part of the present disclosure.

An embodiment provides a system. In one implementation, the system includes but is not limited to a computing device and instructions. The instructions when executed on the computing device cause the computing device to provide a graphical illustration of a first possible outcome of a use of a treatment parameter with respect to at least one body portion, the first possible outcome based on at least one dataset associated with at least one predictive basis, and applying a filter criteria to the at least one dataset to provide a modified graphical illustration of a second possible outcome of the use of the treatment parameter. In addition to the foregoing, other system aspects are described in the claims, drawings, and text forming a part of the present disclosure.

An embodiment provides a graphical user interface. In one implementation, the user interface includes but is not limited to at least a first portion configured to receive a first request to provide a graphical illustration of a first possible outcome of a use of a treatment parameter with respect to at least one body portion, the first possible outcome based on at least one dataset associated with at least one predictive basis, at least a second portion configured to receive a second request to apply a filter criteria to the at least one dataset to provide a modified graphical illustration of a second possible outcome of the use of the treatment parameter, and at least a third portion configured to illustrate the graphical illustration and the modified graphical illustration. In addition to the foregoing, other graphical user interface aspects are described in the claims, drawings, and text forming a part of the present disclosure.

In addition to the foregoing, various other embodiments are set forth and described in the text (e.g., claims and/or detailed description) and/or drawings of the present description.

The foregoing is a summary and thus contains, by necessity, simplifications, generalizations and omissions of detail; consequently, those skilled in the art will appreciate that the summary is illustrative only and is not intended to be in any way limiting. Other aspects, features, and advantages of the devices and/or processes described herein, as defined by the claims, will become apparent in the detailed description set forth herein.

BRIEF DESCRIPTION OF THE DRAWINGS

FIG. 3 illustrates an alternative embodiment of treatment data associated with the clinical system of FIG. 1.

FIG. 5 illustrates another alternative embodiment of treatment data associated with the clinical system of FIG. 1, with specific examples of treatment data.

FIG. 6 illustrates additional alternative embodiments of treatment data associated with the clinical system of FIG. 1, with specific examples of treatment data.

FIG. 7 illustrates additional alternative embodiments of treatment data associated with the clinical system of FIG. 1, with specific examples of treatment data.

The use of the same symbols in different drawings typically indicates similar or identical items.

DETAILED DESCRIPTION

Figure 1:
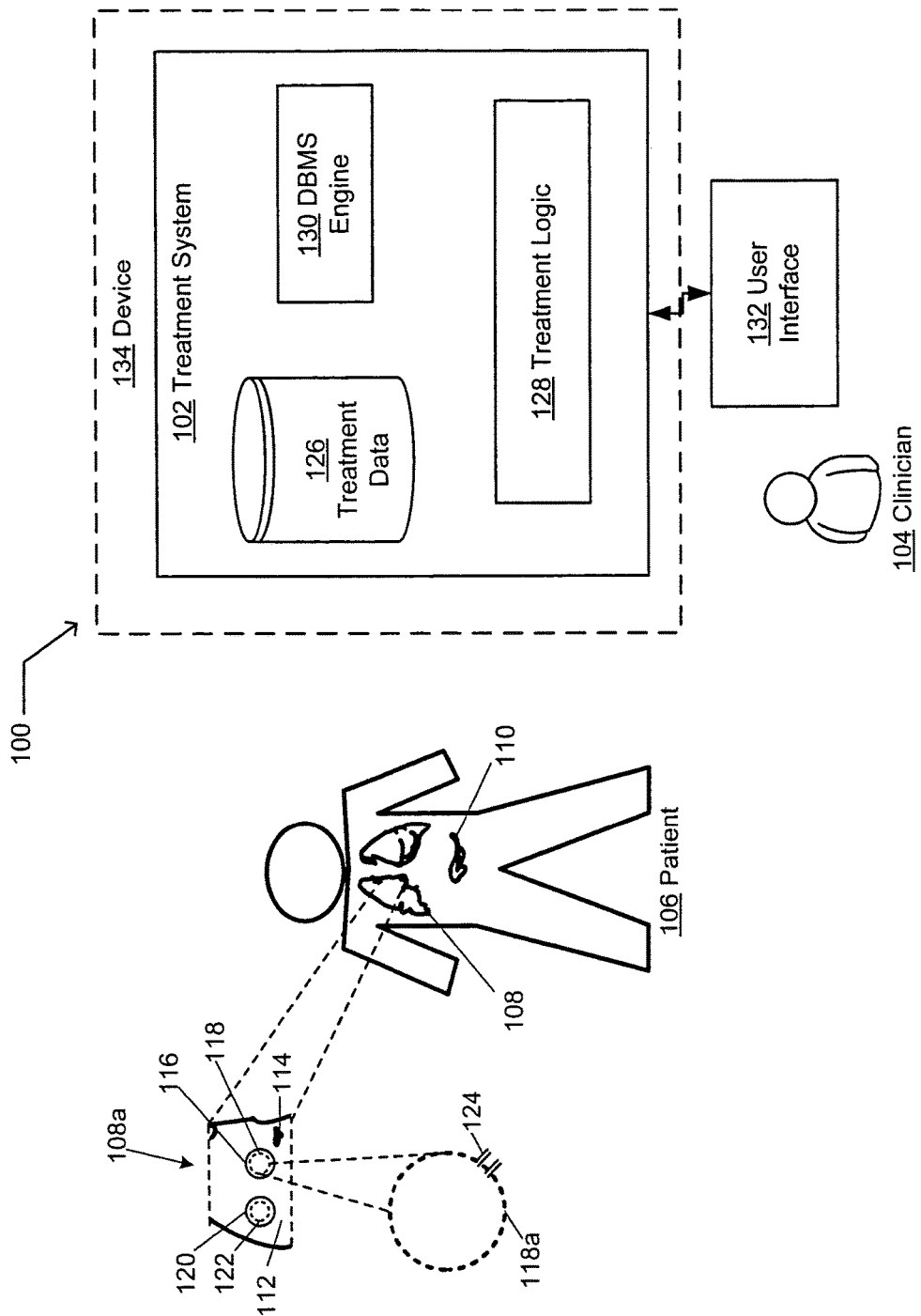
FIG. 1 illustrates an example clinical system in which embodiments may be implemented, perhaps in a device.

FIG. 1 illustrates an example clinical system 100 in which embodiments may be implemented. The clinical system 100 includes a treatment system 102. The treatment system 102 may be used, for example, to store, recall, access, process, implement, or otherwise use information that is beneficial in a clinical setting(s). For example, the treatment system 102 may be used to diagnose or treat patients by storing and/or providing information as to whether or how treatment agent(s) may be applied to a specific region(s) of interest of the human body, such as, for example, a lobe of the lungs, breast tissue, cancerous tissue at a certain bodily location, or other such regions of interest. As a further example, the treatment system 102 may provide information as to whether and/or how to minimize or avoid application of such treatment agents to regions of non-interest (for example, regions to which the treatment agent(s) should not be applied, in order to avoid, e.g., problematic side effects and other undesired results). On the basis of such clinical information, for example, targeted applications of treatment agents (e.g., medication, imaging agents, or other beneficial medical agents) may be carried out in a manner that achieves a desired outcome, while minimizing or eliminating unwanted applications to non-targeted bodily regions.

In FIG. 1, the treatment system 102 is used by a clinician 104. The clinician 104 may, for example, use the treatment system 102 to enter, store, request, or access clinical information such as, for example, the various examples provided herein. The clinician 104 may generally represent, for example, any person involved in health care, including, for example, a doctor, a nurse, a physician's assistant, or a medical researcher. The clinician 104 also may represent someone who is involved in health care in the sense of developing, managing, or implementing the treatment system 102, e.g., a software developer with clinical knowledge (or access to clinical knowledge), a database manager, or an information technologies specialist. Even more generally, some or all of various functions or aspects described herein with respect to the clinician 104 may be performed automatically, e.g., by an appropriately-designed and implemented computing device, or by software agents or other automated techniques.

A patient 106 generally represents any person with an illness, injury, or disease, or who is thought to potentially have such an illness, injury, or disease, or who may be wholly or partially healthy but who is nonetheless studied in order to determine information about such an illness, injury, or disease. The patient 106 also may represent or include other diagnostic and/or animal subjects that may be used in order, for example, to determine an efficacy of a particular medication or treatment, specific examples of which are provided herein. The patient 106 may represent a particular patient in a given clinical setting, such as in a doctor's office, or in a hospital, who is to be diagnosed and/or treated using the treatment system 102. The patient 106 also may represent the more abstract notion of a class of patients (e.g., patients having a certain age, gender, race, genetic makeup, or disposition to illness or disease), or, even more generally, may represent the general notion of a generic patient during basic research and/or development or application of various medical treatments or procedures. In this latter sense, the patient 106 may also represent a non-human animal (such as a primate) believed to be sufficiently similar to a human for the particular purposes that they may usefully substitute for such for the particular purposes.

As such, the patient 106 generally possesses or is associated with, for example, some or all of the various organs, systems, organ systems, organ subsystems, diseased tissue, and/or healthy tissue that may be found in the body. In FIG. 1, the patient 106 is illustrated as having a lung 108 and a pancreas 110, so that these (and other) body parts may be used as the bases for the specific examples given herein. Of course, many other applications of the treatment system 102 exist, over and above the examples provided herein.

In an exploded portion 108a of the lung 108, various example elements are illustrated, although not drawn to scale for the purposes of clarity and ease of illustration and description. For example, the lung 108 may include a healthy tissue portion 112, and a diseased tissue portion 114. The healthy tissue 112 may include, for example, healthy lung tissue, while the diseased tissue 114 may include, for example, a tumor or other cancerous tissue.

The lung 108 also may include a blood vessel 116, which is illustrated in a cut-away view, and which includes a tissue component 118 known as, by way of example nomenclature, the endothelium, endothelial layer, or endothelial cells. The endothelium or endothelial layer 118 generally refers to a layer of cells that lines an interior of a portion of the circulatory system, such as the blood vessel 116. In FIG. 1, the blood vessel 116 and the endothelial layer 118 are illustrated as being in the vicinity of the diseased tissue 114. In contrast, an example of a blood vessel 120 is illustrated that contains endothelial layer 122. The blood vessel 120 is shown as being in the vicinity of the healthy tissue 112 of the lung 108.

Certain properties of the endothelial layer 118 and the endothelial layer 122 may enable the targeted delivery of one or more treatment agents to a vicinity of the diseased tissue 114 and the healthy tissue 112, respectively. For example, blood (and other cells contained therein) will be transported within and along a length of the blood vessel 116, where the length of the blood vessel 116 naturally extends a relatively long distance in either direction toward/away from the diseased tissue 114. However, cells of the endothelial layer 118 that have developed and/or grown over a period of time in a vicinity of the diseased tissue 114 may exhibit characteristics that are unique, or essentially unique, to a site on the endothelial layer 118 in that particular vicinity.

For example, the diseased tissue 114 may include a tumor that has grown over a period of time. During that period of time, a corresponding growth or development of a site on the endothelial layer 118 may reflect, or otherwise be correlated with and/or affected by, the growth of the diseased tissue (tumor) 114. This correlation between the history or ancestry of the site on the endothelial layer 118 in the vicinity of the diseased tissue 114 may result in unique, or almost unique, properties of the tissue ancestry-correlated site, such as, for example, a display of specific and identifiable proteins. Moreover, similar comments may apply to a tissue ancestry-correlated site along the endothelial layer 122 of the blood vessel 120, in the vicinity of the healthy tissue 112. In this way, each such tissue ancestry-correlated site, whether in the lung or in other sites in the body, may be used to provide, effectively, a molecular-level address that specifies a location within the body, e.g., a location of the diseased tissue 114 and/or the healthy tissue 112.

Other mechanisms exist by which such molecular-level addresses, i.e., tissue ancestry-correlated sites, may arise at a given location in the body. For example, such sites may originate in or at a first location in the body, and may thereafter undergo transport to, and engraftment/implantation at, a second location in the body. For example, tissue may originate in bone marrow, or in a distant neoplasm, and may be transported through the vasculature to another, second location in the body (e.g., the lungs 108). Such tissue, which may be, for example, as small as a single cell, may embed at the second location and thereafter serve as a molecular-level address or site to which other agent(s) may bind.

However such tissue ancestry-correlated sites arise, it should be understood from the description provided herein that the tissue ancestry-correlated sites may be used to direct treatment agents (such as, for example, medications, imaging agents, or radio-immunotherapy agents) in a desired fashion. For example, as described in more detail in certain examples provided herein, radionuclides may be applied to the diseased tissue 114.

In this regard, it should be understood that, without use of the tissue ancestry-correlated site(s) described herein, it may be difficult to direct such treatment agents to desired body regions with a necessary or desired level of precision. For example, many treatment agents may be delivered by injection (or by other delivery modalities, e.g., swallowing or absorption through the skin) into a bloodstream of the patient 106. However, without an effective way to direct the treatment agents once in the bloodstream, a positive impact of the treatment agents may be reduced or eliminated. Moreover, ancillary delivery of the treatment agents to undesired regions (e.g., delivery of radionuclides to the healthy tissue 112 and/or to the pancreas 110 or other organs) may result in harm to the patient 106. Such harm may be particularly acute or problematic in cases where, for example, a concentration, dosage, or amount of the treatment agent in the bloodstream is required to be increased relative to an optimal treatment amount, simply to ensure that some portion of the treatment agent reaches and affects a desired end target. Similar comments may apply to other treatment modalities. For example, treatment of the diseased tissue 114 (e.g., a tumor) may be performed by radiation therapy in which the patient is exposed to radiation, and, again, the net effect of such treatment(s) may be negative due to harm caused by the radiation to the healthy tissue 112.

As just described, then, tissue ancestry-correlated sites may exist within and along the endothelial layers 118 and/or 122, in the vicinity of correlated tissues that may serve as target(s) (e.g., the diseased tissue 114) for certain treatment agent(s). For example, these target-related tissue ancestry-correlated sites may include, as described herein, certain proteins that may be known to bind to/with certain other agents. In one specific example discussed herein, a target-related tissue ancestry-correlated binding site includes a protein, aminopeptidase-P (APP), that is known to bind with an agent such as, for example, I-labeled monoclonal antibodies. If a treatment agent (such as, for example, radionuclides) is associated with the target-related tissue ancestry-correlated binding agent (e.g., the I-labeled monoclonal antibodies), then injection of the target-related tissue ancestry-correlated binding agent into the bloodstream will result in delivery of the treatment agent (e.g., radionuclides) to the target-related tissue ancestry-correlated binding site (e.g., APP in the vicinity of the lung 108). That is, as the target-related tissue ancestry-correlated binding agent moves through the bloodstream, the target-related tissue ancestry-correlated binding agent will bind with the target-related tissue ancestry-correlated binding site in the vicinity of the, in this example, diseased tissue 114, thus resulting in effective application of the attached treatment agent in the desired region of the body of the patient 106.

In many cases, delivery of the treatment agent(s) to the vicinity of desired body regions, by delivering the treatment agents to defined sites along a blood vessel wall(s) in the desired vicinity, may be sufficient to obtain a desired result, even if the treatment agents are continually contained within the blood vessel(s) at the target-related tissue ancestry-correlated binding sites. In various cases, treatment agent delivery should occur with greater or lesser levels of specificity and/or efficacy. For example, in some cases, it may be sufficient to provide the treatment agent in the lung 108, while in other cases the treatment agent must or should be applied substantially only to the diseased tissue 114.

Additionally, in some cases, it may be possible and/or desirable to breach or penetrate a wall of the blood vessel(s) 116/120, in order to reach associated tissue(s) directly. For example, in FIG. 1, an enlarged view 118a of the endothelial layer 118 is illustrated that includes a mechanism by which the treatment agents may directly access a direct end target of tissue (e.g., the diseased tissue 114). Specifically, FIG. 1 illustrates a mechanism 124 that may include, for example, structures known as caveolae. Although the mechanism (e.g., caveolae) 124 are shown conceptually in FIG. 1 as tubes or access points, caveolae generally refer to small invaginations of a surface of the blood vessel 116 that carry out certain transport and/or signaling functions between cells within the blood vessel 116 and cells outside of the blood vessel 116 (e.g., the diseased tissue 114). Further discussion regarding caveolae 124 is provided in various examples, herein.

Although many other examples are provided herein and with reference to the various figures, it should be understood that many types and instances of treatment data may play a role in the use and application of the various concepts referenced above and described in more detail herein. The treatment system 102 may store such treatment data 126 in a database or other memory, for easy, convenient, and effective access by the clinician 104.

The treatment data 126 may include, for example, not only the target-related tissue ancestry-correlated binding site(s) and/or the related target-related tissue ancestry-correlated binding agent(s), but also various other parameters and/or characteristics related to treatment of the patient 106, examples of which are provided herein. Through detailed storage, organization, and use of the treatment data 126, the clinician 104 may be assisted in determining optimal treatment techniques for the patient 106, in order, for example, to select and deliver an appropriate type and/or level of a treatment agent, with an appropriate degree of accuracy, to a desired end target (based on an appropriate target-related tissue ancestry-correlated binding site and/or an appropriate target-related tissue ancestry-correlated binding agent), while minimizing any negative impact of such a selection/delivery, if any, on other regions of the body of the patient 106. Ordered assignment and/or storage of information within the treatment data 126, as described herein, facilitates and/or enables such recall, access, and/or use of the treatment data by the clinician 104 in treating the patient 106.

In the treatment system 102, treatment logic 128 may be used to store, organize, access, recall, or otherwise use the information stored in the treatment data 126. For example, the treatment logic 128 may access a database management system (DBMS) engine 130, which may be operable to perform computing operations to insert or modify new data into/within the treatment data 126, perhaps in response to new research or findings, or in response to a preference of the clinician 104. For example, if a new treatment agent is discovered to be effective on the diseased tissue 114, the clinician 104 may access the treatment system 102 using a user interface 132, in order to use the DBMS engine 130 to associate the new treatment agent with one or more instances of the target-related tissue ancestry-correlated binding site(s) and/or target related tissue ancestry-correlated binding agent(s) that may be known to be useful in targeting the diseased tissue 114, within the treatment data database 126 (assuming that the treatment agent is suitable for direct or indirect delivery via the target-related tissue ancestry-correlated binding agent, as described herein). As another example, if a new target-related tissue ancestry-correlated binding site is identified in the endothelial layer 118 in the vicinity of the diseased tissue 114, then this new target-related tissue ancestry-correlated binding site may be associated with one or more instances of a target-related tissue ancestry-correlated binding agent, e.g., there may be more than one agent that is useful in attaching to the new target-related tissue ancestry-correlated binding site for delivery of one or more treatment agents.

Similarly, in a case where the clinician 104 seeks, for example, to diagnose or treat the patient 106, the clinician 104 may access the user interface 132 to use the treatment logic 128 and/or the DBMS Engine 130 to determine best known methods or treatments to be applied in a given clinical scenario. For example, if the patient 106 has a certain type of disease or illness in a certain region of the body, then the clinician may input this information via the user interface 132 in order to obtain one or more options for treating the disease or illness. For example, if the patient 106 exhibits the diseased tissue 114, then the clinician 104 may select the (type of) diseased tissue 114 in the lung 108 as an end target, and the treatment logic 128 may then interface with the DBMS engine 130 to obtain, from the treatment data 126, one or more options for providing the treatment agent to the diseased tissue 114, e.g., one or more target-related tissue ancestry-correlated binding sites (such as, for example, two different proteins that are expressed or displayed in the endothelial layer 118 in the vicinity of the diseased tissue 114). As another example, if the clinician 104 is already aware of a target-related tissue ancestry-correlated binding site in the vicinity of the diseased tissue 114, then the clinician 104 may input this information into the treatment system 102 and be provided with one or more, for example, target-related tissue ancestry-correlated binding agents that may be known to attach to the known target-related tissue ancestry-correlated binding site.

In this regard, it should be understood that multiple instances of a target-related tissue ancestry-correlated binding site, as described, may be present at any one location in the body, and, moreover, virtually any region or site in the body having a blood-tissue interface may also exhibit an associated, target-related tissue ancestry-correlated binding site. Further, new instances of target-related tissue ancestry-correlated binding sites may be discovered and/or approved for clinical use on a relatively frequent basis. Still further, there may be many different treatment parameters and/or characteristics that may be related to the various target-related tissue ancestry-correlated binding site(s) and/or target-related tissue ancestry-correlated binding agent(s), such as, for example, treatment agents and/or delivery mechanisms.

As a result, the clinician 104, e.g., a physician in the field, may not be aware of all currently-available content of the treatment data 126. Thus, the treatment system 102 provides the clinician with readily-available, accurate, current, and/or comprehensive treatment information, and also provides techniques to ensure that the treatment information remains accurate, current, and/or comprehensive, by allowing the addition and/or modification of the existing treatment data 126, as new treatment information becomes available.

In FIG. 1, the treatment system 102 is illustrated as possibly being included within a device 134. The device 134 may include, for example, a mobile computing device, such as a personal digital assistant (PDA), or a laptop computer. Of course, virtually any other computing device may be used to implement the treatment system 102, such as, for example, a workstation, a desktop computer, or a tablet PC.

Additionally, not all of the treatment system 102 need be implemented on a single computing device. For example, the treatment data 126 may be stored on a remote computer, while the user interface 132 and/or treatment logic 128 are implemented on a local computer. Further, aspects of the treatment system 102 may be implemented in different combinations and implementations than that shown in FIG. 1. For example, functionality of the DBMS engine 130 may be incorporated into the treatment logic 128 and/or the treatment data 126.

The treatment data 126 may be stored in virtually any type of memory that is able to store and/or provide access to information in, for example, a one-to-many, many-to-one, and/or many-to-many relationship. Such a memory may include, for example, a relational database and/or an object-oriented database, examples of which are provided in more detail herein.

Figure 2:
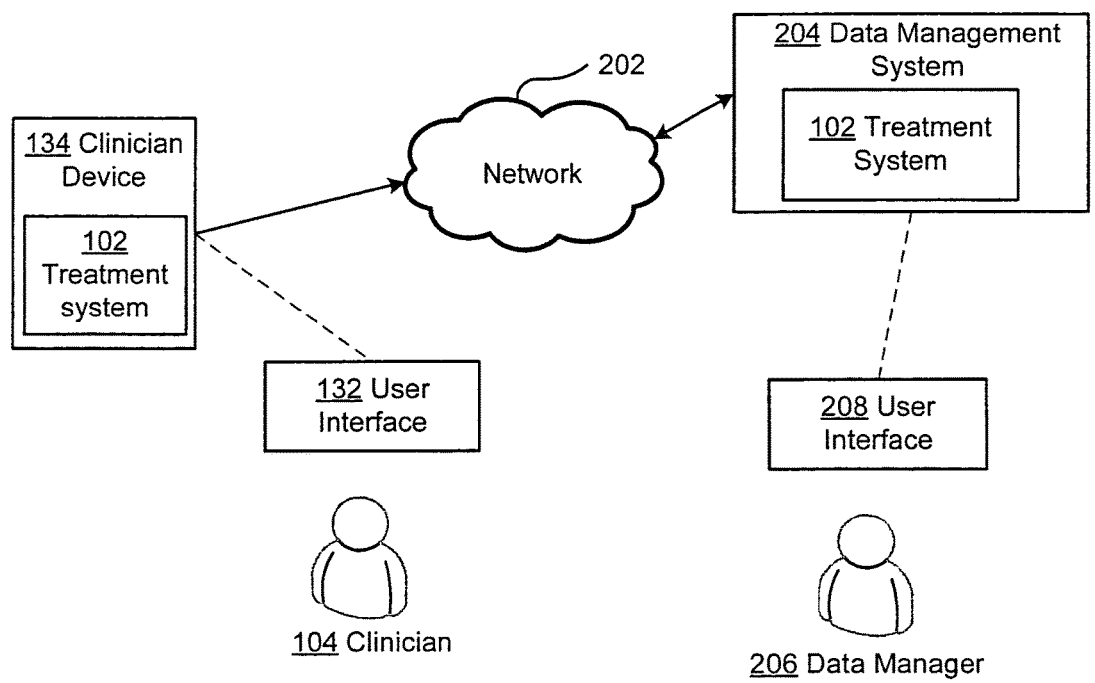
FIG. 2 illustrates certain alternative embodiments of the clinical system of FIG. 1.

FIG. 2 illustrates certain alternative embodiments of the clinical system 100 of FIG. 1. In FIG. 2, the clinician 104 uses the user interface 132 to interact with the treatment system 102 deployed on the clinician device 134. The clinician device 134 is in communication over a network 202 with a data management system 204, which is also running the treatment system 102; the data management system 204 may be interacted with by a data manager 206 through a user interface 208. Of course, it should be understood that there may be many clinicians other then the specifically-illustrated clinician 104, each with access to an individual implementation of the treatment system 102. Similarly, multiple data management systems 204 may be implemented.

In this way, the clinician 104, who may be operating in the field, e.g., in an office and/or hospital environment, may be relieved of a responsibility to update or manage contents in the treatment data 126, or other aspects of the treatment system 102. For example, the data management system 204 may be a centralized system that manages a central database of the treatment data 126, and/or that deploys or supplies updated information from such a central database to the clinician device 134.

FIG. 3 illustrates an alternative embodiment of the treatment data 126 associated with the clinical system 100 of FIG. 1. In FIG. 3, and in the various examples herein, a particular nomenclature is used for the terms described above and related terms, in order to provide consistency and clarity of description. However, it should be understood that other terminology may be used to refer to the same or similar concepts.

In FIG. 3, treatment parameters 302 are stored and organized with respect to a plurality of treatment characteristics 304. The treatment characteristics 304 include many of the terms and concepts just described, as well as additional, but not exhaustive, terms and concepts that may be relevant to a use and operation of the treatment system 102.

For example, the treatment characteristics 304 include a direct end target 306. The direct end target 306 may refer, for example, to any tissue, organ, organ system, organ subsystem (or type thereof), or any other body part or region that may be targeted for healing, destruction, repair, enhancement, and/or imaging that may be targeted—directly or indirectly—via an associated target-related tissue ancestry-correlated binding site 314 and/or an associated tissue related tissue ancestry-correlated binding agent 316 and/or an associated treatment agent delivery mechanism relative to the target-related tissue ancestry-correlated binding agent 318 and/or an associated treatment agent 320. A discriminated end target 308 refers to targets that should be avoided during implementation of the healing, destruction, repair, enhancement and/or imaging actions that may be discriminated—directly or indirectly—via an associated target-related tissue ancestry-correlated binding site 314 and/or an associated tissue related tissue ancestry-correlated binding agent 316 and/or an associated treatment agent delivery mechanism relative to the target-related tissue ancestry-correlated binding agent 318 and/or an associated treatment agent 320. For example, in FIG. 1, the lung 108 may include the direct end target 306 as the diseased tissue 114, and may include the discriminated end target 308 as the healthy tissue 112, and/or the pancreas 110.

Somewhat analogously, a direct intermediate target 310 refers to targets that are connected to, associated with, or in the vicinity of the direct end target that may be targeted via an associated target-related tissue ancestry-correlated binding site 314 and/or an associated tissue related tissue ancestry-correlated binding agent 316 and/or an associated treatment agent delivery mechanism relative to the target-related tissue ancestry-correlated binding agent 318 and/or an associated treatment agent 320. For example, a portion of the endothelial layer 118 in a vicinity of the diseased tissue 114 (or other end target) may act as a direct intermediate target 310. Then, a discriminated intermediate target 312 may refer to endothelial tissue of the layer 118 that is not in a vicinity of the diseased tissue 114 that may be discriminated via an associated target-related tissue ancestry-correlated binding site 314 and/or an associated tissue related tissue ancestry-correlated binding agent 316 and/or an associated treatment agent delivery mechanism relative to the target-related tissue ancestry-correlated binding agent 318 and/or an associated treatment agent 320.

As already referenced, a target-related tissue ancestry-correlated binding site 314 refers to a determined chemical and/or genetic and/or biological structure to which various chemical compounds and/or genes may be affixed. For example, the target-related tissue ancestry-correlated binding site 314 may include a specific protein that is displayed at the endothelial layer 118 in a vicinity of the diseased tissue 114. The target-related tissue ancestry-correlated binding site 314 may be selectively associated with the direct end target 306 either directly or through the direct intermediate target 310.

A target-related tissue ancestry-correlated binding agent 316, then, may refer to some specific chemical and/or genetic and/or biological structure that more or less selectively binds or attaches to a related one of the target-related tissue ancestry-correlated binding sites 314. The target-related tissue ancestry-correlated binding agent 316 also may be associated with a treatment agent delivery mechanism relative to the target-related tissue ancestry-correlated binding agent 318, which may refer either to something that may be directly attached to (or associated with) the target-related tissue ancestry-correlated binding agent 316, and/or something that may be attached to (or associated with) one or more intermediary or indirect structures that attach to the target-related tissue ancestry-correlated binding agent 316 and that act to house and/or deliver a treatment agent 320. As an example of the intermediary or indirect structures just referenced, a nano-container may be used that dissolves and/or otherwise opens in a vicinity of the target-related tissue ancestry-correlated binding site 314, and thereby releases and/or delivers the treatment agent 320 included inside.

The treatment agent 320 thus binds/attaches to, or otherwise is associated with, either directly or indirectly, the target-related tissue ancestry-correlated binding agent 316. Thus, as described, the treatment agent 320 may be effectively transported to the appropriate direct intermediate target 310 and thereby to the target-related tissue ancestry-correlated binding site 314. In this way, the treatment agent 320 may be delivered to the direct end target 306 (or at least to a vicinity of the direct end target 306), while not being delivered either to the discriminated intermediate target(s) 312 and/or the discriminated end target(s) 308.

FIG. 3 thus illustrates that there may be many different relationships or associations between any one (or more) of the treatment characteristics 304. For example, one or more instances of any one or more of the treatment characteristics 304 may be considered to be one of the treatment parameters 302, and thereafter associated with one or more instances of the remaining treatment characteristics 304. For example, the direct end target 306 may be considered to be the treatment parameter(s) 302, where a first instance 302a of the direct end target 306 may refer to diseased lung tissue, and the second instance 302b may refer to diseased breast tissue, and both instances may be associated with an instance of the target-related tissue ancestry-correlated binding agent 316. Similarly, two or more instances of the target-related tissue ancestry-correlated binding agent 316 (e.g., I-labeled APP monoclonal antibodies targeted on two different antigens) may be associated with one treatment agent 320 (e.g., radio-immunotherapy via application of low levels of radionuclides).

Many other examples of relationships and associations between the various treatment parameters 302 and/or the treatment characteristics 304 (and/or other treatment information) may be defined or determined and stored in the treatment data 126 according to the treatment logic 128. Certain of these examples are provided herein.

Additionally, although the treatment data 126 is illustrated conceptually in FIG. 3 as a flat table in which one or more of the selected treatment parameters 302 are associated with one or more of the treatment characteristics, it should be understood that this illustration is for explanation and example only, and is not intended to be limiting in any way with respect to the various ways in which the treatment data 126 may be stored, organized, accessed, recalled, or otherwise used.

For example, the treatment data 126 may be organized into one or more relational databases. In this case, for example, the treatment data 126 may be stored in one or more tables, and the tables may be joined and/or cross-referenced in order to allow efficient access to the information contained therein. Thus, the treatment parameter(s) 302 may define a record of the database(s) that is associated with various ones of the treatment characteristics 304.

In such cases, the various tables may be normalized so as, for example, to reduce or eliminate data anomalies. For example, the tables may be normalized to avoid update anomalies (in which the same information would need to be changed in multiple records, and which may be particularly problematic when treatment data database 126 is large), deletion anomalies (in which deletion of a desired field or datum necessarily but undesirably results in deletion of a related datum), and/or insertion anomalies (in which insertion of a row in a table creates an inconsistency with another row(s)). During normalization, an overall schema of the database may be analyzed to determine issues such as, for example, the various anomalies just referenced, and then the schema is decomposed into smaller, related schemas that do not have such anomalies or other faults. Such normalization processes may be dependent on, for example, desired schema(s) or relations between the treatment parameters 302 and/or treatment characteristics 304, and/or on desired uses of the treatment data 126.

Uniqueness of any one record in a relational database holding the treatment data 126 may be ensured by providing or selecting a column of each table that has a unique value within the relational database as a whole. Such unique values may be known as primary keys. These primary keys serve not only as the basis for ensuring uniqueness of each row (e.g., treatment parameter) in the database, but also as the basis for relating or associating the various tables within one another. In the latter regard, when a field in one of the relational tables matches a primary key in another relational table, then the field may be referred to a foreign key, and such a foreign key may be used to match, join, or otherwise associate (aspects of) the two or more related tables.

FIG. 3 and associated potential relational databases represent only one example of how the treatment data may be stored, organized, processed, accessed, recalled, and/or otherwise used.

Figure 4:
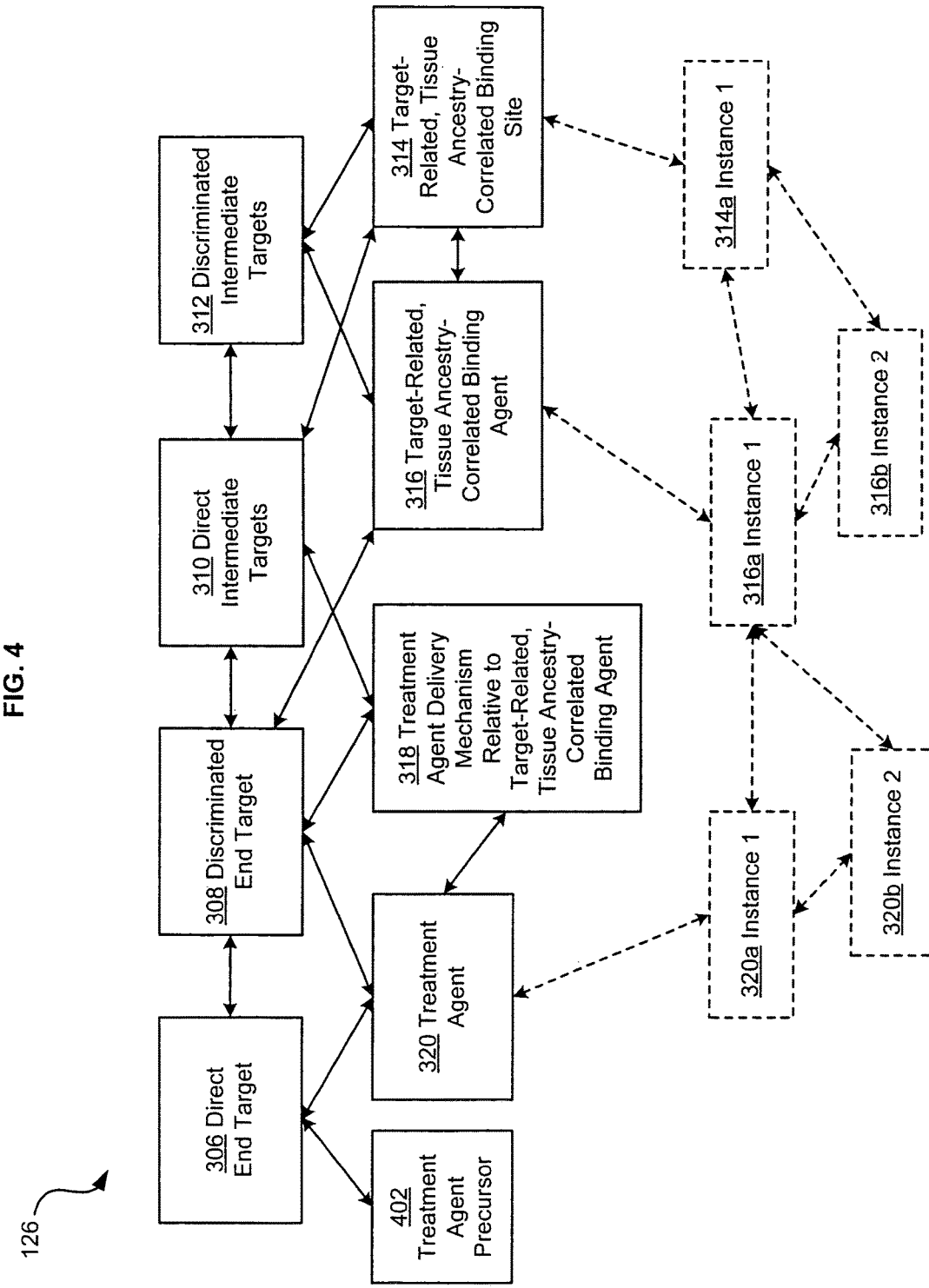
FIG. 4 illustrates another alternative embodiment of treatment data associated with the clinical system of FIG. 1.

FIG. 4 illustrates another alternative embodiment of treatment data 126 associated with the clinical system 100 of FIG. 1, in which the treatment data 126 is conceptually illustrated as being stored in an object-oriented database.

In such an object-oriented database, the various treatment parameter(s) 302 and/or treatment characteristic(s) 304, and/or instances thereof, may be related to one another using, for example, links or pointers to one another. FIG. 4 illustrates a conceptualization of such a database structure in which the various types of treatment data are interconnected, and is not necessarily intended to represent an actual implementation of an organization of the treatment data 126.

The concepts described above may be implemented in the context of the object-oriented database of FIG. 4. For example, two instances 320a and 320b of the treatment agent 320 may be associated with one (or more) instance 316a of the target-related tissue ancestry-correlated binding agent 316. Meanwhile, two instances 316a and 316b of the target-related tissue ancestry-correlated binding agent 316 may be associated with an instance 314a of the target-related tissue ancestry-correlated binding site 314.

Also, other data may be included in the treatment data 126. For example, in FIG. 4, a treatment agent precursor 402 is shown that refers generally to an agent used to facilitate application of the treatment agent 320, e.g., an immune-response element that is used to identify/mark/bond with the target-related tissue ancestry-correlated binding site 314 and/or a substance that when metabolized becomes treatment agent 320, such as with prodrugs.

Many other examples of databases and database structures also may be used. Other such examples include hierarchical models (in which data are organized in a tree and/or parent-child node structure), network models (based on set theory, and in which multi-parent structures per child node are supported), or object/relational models (combining the relational model with the object-oriented model).

Still other examples include various types of extensible Mark-up Language (XML) databases. For example, a database may be included that holds data in some format other than XML, but that is associated with an XML interface for accessing the database using XML. As another example, a database may store XML data directly. Additionally, or alternatively, virtually any semi-structured database may be used, so that context may be provided to/associated with stored data elements (either encoded with the data elements, or encoded externally to the data elements), so that data storage and/or access may be facilitated.

Such databases, and/or other memory storage techniques, may be written and/or implemented using various programming or coding languages. For example, object-oriented database management systems may be written in programming languages such as, for example, C++ or Java. Relational and/or object/relational models may make use of database languages, such as, for example, the structured query language (SQL), which may be used, for example, for interactive queries for information and/or for gathering and/or compiling data from the relational database(s).

As referenced herein, the treatment system 102 may be used to perform various data querying and/or recall techniques with respect to the treatment data 126, in order to facilitate treatment and/or diagnosis of the patient 106. For example, where the treatment data are organized, keyed to, and/or otherwise accessible using one or more of the treatment parameters 302 and/or treatment characteristics 304, various Boolean, statistical, and/or semi-Boolean searching techniques may be performed.

For example, SQL or SQL-like operations over one or more of the treatment parameters 302/treatment characteristics 304 may be performed, or Boolean operations using the treatment parameters 302/treatment characteristics 304 may be performed. For example, weighted Boolean operations may be performed in which different weights or priorities are assigned to one or more of the treatment parameters 302/treatment characteristics 304, perhaps relative to one another. For example, a number-weighted, exclusive-OR operation may be performed to request specific weightings of desired (or undesired) treatment data to be included (excluded).

For example, the clinician 104 may wish to determine examples of the direct end target 306 that are associated with examples of the discriminated end target 308 that are highly discriminated against with respect to delivery of the target-related tissue ancestry-correlated binding agent 316, for highly-specific delivery of the treatment agent 320. For example, the clinician 104 may want to know instances of the treatment agent 320 that may be delivered to the lungs as the direct end target 306, without substantially affecting the pancreas, liver, or other tissue, organ, or organ system/subsystem. In other examples, the clinician may be willing to tolerate lower levels of discrimination (e.g., increased delivery of the treatment agent 320 to other body regions), perhaps because the patient 106 is in an advanced stage of illness. As another example, the clinician 104 may start with a preferred (type of) the treatment agent 320, and may request from the treatment system 102 various delivery techniques (e.g., target-related tissue ancestry-correlated binding agent 316) that may be available, perhaps with varying levels of efficacy.

The clinician 104 may specify such factors using, for example, the user interface 132. For example, the clinician 104 may be able to designate one or more of the treatment parameters 302/treatment characteristics 304, and assign a weight or importance thereto, using, for example, a provided ranking system. In this regard, and as referenced herein, it should be understood that the clinician 104 may wish to deliver a particular instance of the treatment agent 320, e.g., a particular radionuclide to be delivered to a tumor. However, such a treatment agent, if applied by conventional techniques, may be problematic or prohibited (e.g., where a current physiological condition of the patient 106 and/or state of an immune system of the patient 106 is insufficient to allow the clinician 104 to use the desired treatment agent). Moreover, the clinician 104 may not be aware that a suitable target-related tissue ancestry-correlated binding site 314 and/or target-related tissue ancestry-correlated binding agent 316 has (have) been discovered for delivering the treatment agent with a desired/required level of accuracy. However, the clinician 104 may query the treatment system 102 based on the desired treatment agent 320, and may thereby discover the technique(s) by which the treatment agent may be applied, and with the necessary level of specificity.

Similarly, data analysis techniques (e.g., data searching) may be performed using the treatment data 126, perhaps over a large number of databases. For example, the clinician 104 may perform a physical screening of the patient 106, and may input some body system, tissue, organ, or organ system/subsystem parameters against which screening is to be performed. Then, the clinician should receive a listing of target-related tissue ancestry-correlated binding sites and/or target-related tissue ancestry-correlated binding agents that are ranked according to some criteria. For example, the clinician 104 may receive a listing of instances of the target-related tissue ancestry-correlated binding site 314 that provide a particularly high or low level of discrimination with respect to a particular direct end target 306, discriminated end target 308, and/or treatment agent 320. In this way, for example, if the patient 106 has an organ or organ subsystem that requires protection from a given instance of the treatment agent 320, then the clinician 104 may select an instance of the target-related tissue ancestry-correlated binding site 314 and/or of the target-related tissue ancestry-correlated binding agent 316 accordingly, even if some relative sacrifice of binding strength/accuracy is associated with such a selection.

By way of further example, other parameters/characteristics may be factored in. For example, elimination pathways may be tracked, databased, and/or weighted for use in the treatment data 126 and/or the treatment system 102. For example, if a particular instance of the target-related tissue ancestry-correlated binding agent is especially readily eliminated by the liver, then, in a case where the patient 106 has impaired hepatic function, such an instance may be selected for delivering the treatment agent 320, even if an otherwise superior instance of the target-related tissue ancestry-correlated binding agent 316 is known. Algorithms implementing such query/recall/access/searching techniques may thus use Boolean or other techniques to output, for example, a thresholded, rank-ordered list. The treatment logic 128 may then assign a key or other identifier to such a list(s), for easier use thereof the next time a like query is performed.

Design and testing of querying techniques in particular implementations of the treatment system 102 may involve, for example, entry of candidate treatment parameters 302/treatment characteristics 304 (or instances thereof) into a database(s), along with associated test results and/or affinity metrics that may be used to determine/weight targets or sets of targets. Then, an identifier may be generated that is unique to the target(s) set(s).

Still other examples/applications include avoiding an auto-immune response of the patient 106, in order to achieve a desired result. For example, the treatment system 102 may be used to determine/catalog/use treatment data that relates to treatment parameters 302/treatment characteristics 304 that are known or suspected to avoid self-epitopes (i.e., those unlikely to generate an undesired autoimmune response). FIG. 5 illustrates another alternative embodiment of treatment data associated with the clinical system 100 of FIG. 1, with specific examples of treatment data. In particular, all of FIGS. 5-7 provide or refer to example results from related technical papers, which are specifically referenced below.

For example, rows of the table of FIG. 5 (e.g., rows 502, 504, and 506, respectively) refer to examples that may be found in Oh, P. et al., "Subtractive Proteomic Mapping of the Endothelial Surface in Lung and Solid Tumours for Tissue-Specific Therapy," Nature, vol. 429, pp. 629-635 (Jun. 10, 2004), which is hereby incorporated by reference in its entirety, and which may be referred to herein as the Oh reference.

In the Oh reference, it is generally disclosed that regions of endothelium may change or alter over time, based on what tissues are in the vicinity thereof, as referenced herein. The Oh reference, for example, identified lung-induced and/or lung-specific endothelial cell surface proteins based on a hypothesis that a surrounding tissue (micro) environment of the endothelial cell surface proteins modulates protein expression in the vascular endothelium. The Oh reference identified specific proteins that were found to be expressed at an endothelial surface by specifying two regions of interest (e.g., a "lung region" and a "non-lung region"), and then determining proteins within the two regions. Then, by subtracting the two sets of proteins from one another, non-common proteins were identified.

In this way, uniquely occurring proteins at a specific endothelial site (e.g., the target-related tissue ancestry-correlated binding site 314 at a specific direct intermediate target 310) were identified. Then, these uniquely-occurring proteins were used as targets for generated antibodies. As a result, it was possible to target, for example, lung-specific tissues as opposed to non-lung-specific tissues, and/or to target tumors as opposed to non-tumor tissues. More specifically, for example, it was determined to be possible to target tumor-induced endothelial cell proteins (e.g., target-related tissue ancestry-correlated binding sites 314) for delivery thereto of drugs, imaging agents, and/or radiation agents (e.g., treatment agents 320) that were attached to appropriate antibodies (target-related tissue ancestry-correlated binding agents 316).

Thus, to set forth specific examples, a row 502 illustrates an example in which the direct end target 306 includes a treatment parameter of "lung tissue." In this example, the discriminated end target 308 includes "non-lung tissue." The direct intermediate target 310 includes endothelial tissues that are proximate to the lung tissue, while the discriminated intermediate target 312 includes endothelial tissue that is proximate to the non-lung tissue.

The target-related tissue ancestry-correlated binding site 314 in this example includes aminopeptidase-P (APP), which is a protein that was detected substantially only in endothelial plasma membranes from the lung tissue (e.g., direct end target 306). In order to take advantage of the immuno-accessibility of APP in vivo, $I^{125}$-labeled monoclonal antibodies were used as the target-related tissue ancestry-correlated binding agent 316, and were intravenously injected into test rats. Subsequent imaging of the lungs illustrated rapid and specific targeting of APP antibody to the lung (e.g., direct end target 306), with significantly reduced accumulation of the injected dose at non-lung tissue (e.g., the discriminated end target 308). Thus, by selecting the treatment agent 320 to include radio-immunotherapy via low levels of radionuclides (e.g., 100 μCi of $I^{125}$), a treatment agent delivery mechanism relative to target-related tissue ancestry-correlated binding agent 318 may involve essentially direct delivery, in that the radionuclide(s) may be affixed to the monoclonal APP antibodies, similarly to how the $I^{125}$ was affixed as described in Oh, et al. Further, although the term antibody is used herein in various examples, it should be understood that other immuno-reactive features of the adaptive immune system also may be used in a similar or analogous manner, including entities that serve to mediate antibody generation, such as, for example, helper T cells or dendritic cells.

In the row 504 of FIG. 5, a conceptual secondary example drawn from/based on the Oh reference is included, in order to illustrate various concepts described herein, e.g., with respect to FIGS. 1-4. Specifically, in the row 504, various ones of the treatment parameters and/or treatment characteristics are the same as in the row 502, except that a second example of the target-related tissue ancestry-correlated binding agent 316 is illustrated generically as "Binding Agent X," and, similarly, a second example of a generically-referenced treatment agent 320 is illustrated as "Treatment Agent X." As such, the row 504 illustrates, for example, that two separate instances of the target-related tissue ancestry-correlated binding agent 316 and/or the treatment agent 320 may be associated with, e.g., an instance of either the direct end target 306, and/or with an instance of the target-related tissue ancestry-correlated binding site 314.

The row 506 illustrates another example from the Oh reference. In the row 506, the direct end target 306 is illustrated as "diseased lung tissue," while the discriminated end target 308 is illustrated as "non-diseased lung tissue." Thus, the direct intermediate target 310 is illustrated as "endothelial tissue proximate to the diseased lung tissue," while the discriminated intermediate target 312 is illustrated as "endothelial tissue that is proximate to non-diseased lung tissue."

Then, the target-related tissue ancestry-correlated binding site 314 is illustrated as fifteen differentially-expressed proteins (e.g., expressed according to the subtractive techniques described herein) associated with the direct intermediate target 310, e.g., the endothelial tissue proximate to the diseased lung tissue. As a result, the target-related tissue ancestry-correlated binding agent 316 is selected and illustrated as I-labeled monoclonal APP antibodies that may be generated for one or more of the fifteen differentially-expressed proteins. As in the row 502, the treatment agent delivery mechanism relative to target-related tissue ancestry-correlated binding agent 318 may involve essentially direct attachment of the treatment agent 320 that is illustrated as radio-immunotherapy via low-levels of radionuclides. In this way, such radionuclides may be concentrated in, and may thereby destroy, tumors. In particular, for example, an identified tumor target was the 34 KDa protein recognized by annexin A1 (AnnA1) antibodies, which was significantly present in substantially only in tumor endothelial plasma membrane.

FIG. 6 illustrates additional alternative embodiments of treatment data associated with the clinical system 100 of FIG. 1, with specific examples of treatment data. In FIG. 6, a row 602 illustrates examples that may be found in Essler et al., "Molecular Specialization of Breast Vasculature: A Breast-Homing Phage-Displayed Peptide Binds to Aminopeptidase P in Breast Vasculature," Proceedings of the National Academy of Sciences, vol. 99, No. 4, pp. 2252-2257 (Feb. 19, 2002), which is hereby incorporated by reference in its entirety, and which may be referred to herein as the Essler reference.

In the Essler reference, a plurality of peptides (e.g., two or more amino acids joined together via a peptide bond) having a general structure of CX7C (where C is cysteine and X is any amino acid) I-labeled monoclonal antibodies were injected into mice. Then tissues of interest were observed to determine a presence of phage(s), and thereby to determine which peptide of the plurality of peptides honed in on the observed tissue(s). In this way, it was determined that the CPGPEGAGC peptide was useful in providing a homing point for phages of the patient's immune system, and, in particular, was useful as a binding agent for the breast tissue, while not binding to pancreas tissue. Although these specific examples of peptides are provided for illustration and explanation, it should be understood that the term peptide as used herein may refer to virtually any lineal peptide-bonded string of amino acid residues, which include various structures thereof, unless context dictates otherwise. For example, a lipopeptide may be interpreted to include virtually all lipoproteins, while glycopeptides may include virtually all glycoproteins.

Thus, in the row 602, the direct end target 306 is illustrated as breast tissue, while the discriminated end target 308 is illustrated as pancreas tissue. The direct intermediate target 310 is illustrated as vascular beds of breast tissue, while the discriminated intermediate target 312 is illustrated as vascular beds of pancreas tissue.

The target-related tissue ancestry-correlated binding site 314 includes a protein, aminopeptidase-P (APP), of the vascular bed of breast tissue. The target-related tissue ancestry-correlated binding agent 316 includes a cyclic nonapeptide known as the CPGPEGAGC peptide, which is shown in the Essler paper to home to the aminopeptidase P receptor. The treatment agent precursor 402 is shown to include phages, which were essentially directly delivered via the CPGPEGAGC peptide to the APP of the vascular bed of breast tissue, and which facilitate attachment of additional/alternative treatment agents 320 to the APP.

A row 604 of FIG. 6 illustrates an example from Hood et al., "Tumor Regression by Targeted Gene Delivery to the Neovasculature," Science, vol. 296, pp. 2404-2407 (Jun. 28, 2002), which is incorporated by reference in its entirety and which is referred to herein as the Hood reference. The Hood reference refers to the molecule integrin avB3 that plays a role in endothelial cell survival during formation of new blood vessels in a given region, and is preferentially expressed therein. A cationic polymerized lipid-based nanoparticle was synthesized and covalently coupled to a small organic avB3 ligand; that is, the ligand was demonstrated to serve as a binding agent for the integrin avB3 that is preferentially expressed in endothelial cells.

Accordingly, in the row 604, melanoma tumors were used as the direct end target 306, while the discriminated end target 308 is shown as surrounding non-tumor tissues. The direct intermediate target 310 is illustrated as endothelial cells having integrin avB3, while the discriminated intermediate target 312 is shown as endothelial cells without integrin avB3. Thus, the target-related tissue ancestry-correlated binding site 314 is shown to include the integrin avB3, while the target-related tissue ancestry-correlated binding agent 316 is shown to include the avB3 ligand that attaches to the integrin avB3. The treatment agent 320 included a gene selected to disrupt formation of new blood vessels in the tumor(s), which was delivered using the cationic polymerized lipid-based nanoparticle(s), and which thereby deprived the tumor(s) of blood and destroyed the tumor(s).

FIG. 7 illustrates additional embodiments of treatment data associated with the clinical system 100 of FIG. 1, with specific examples of treatment data. In a row 702, an example is illustrated from McIntosh et al., "Targeting Endothelium and Its Dynamic Caveolae for Tissue-Specific Transcytosis in vivo: A Pathway to Overcome Cell Barriers to Drug and Gene Delivery," Proceedings of the National Academy of Sciences, vol. 99, no. 4, pp. 1996-2001 (Feb. 19, 2002), which is hereby incorporated by reference and which may be referred to herein as the McIntosh reference. In the McIntosh reference, endothelial cell plasma membranes from the lungs were analyzed to determine monoclonal antibodies targeted thereto. Additionally, the McIntosh reference illustrated use of the caveolae 124 to allow the treatment agent 320 to cross the endothelium and be delivered directly to lung tissue.

Thus, in the row 702, the direct end target 306 is shown as lung tissue, while the discriminated end target 308 is shown as non-lung tissue. The direct intermediate target 310 is shown as endothelial cell caveolae proximate to the lung tissue, while the discriminated intermediate target 312 is shown as endothelial cell caveolae that is distal from the lung tissue.

The target-related tissue ancestry-correlated binding site 314 is shown as a determined/selected antigen to which the monoclonal antibody TX3.833 binds, so that the target-related tissue ancestry-correlated binding agent 316 is shown as the monoclonal antibody TX3.833 itself. In this way, the treatment agent 320 of gold affixed directly to the TX3.833 antibody was transported over the endothelial plasma membrane into the tissues of interest (e.g., lung tissues); in other words, the caveolae 124 was used to conduct transcytosis.

A row 704 illustrates an example from Zhiwei et al., "Targeting Tissue Factor on Tumor Vascular Endothelial Cells and Tumor Cells for Immunotherapy in Mouse Models of Prostatic Cancer," Proceedings of the National Academy of Sciences, vol. 98, no. 21, pp. 12180-12185 (Oct. 9, 2001), which is hereby incorporated by reference in its entirety, and which may be referred to as the Zhiwei reference. In the Zhiwei reference, a "tissue factor" is identified as a transmembrane receptor that forms a strong and specific complex with an associated ligand, factor VII (fVII). Such tissue factor, although not normally expressed on endothelial cells, may be expressed on tumor endothelial cells of the tumor vasculature.

Thus, in the example of the row 704, the direct end target 306 includes prostate tumors, while the discriminated end target 308 includes all other tissues. The direct intermediate target 310 includes tissue factor(s) expressed by/on endothelial cells near the tumor(s) and by/on the tumor itself. The target-related tissue ancestry-correlated binding site 314 includes the tissue factor, while the target-related tissue ancestry-correlated binding site agent 316 includes the factor VII (fVI), the ligand for the tissue factor. In this way, the direct treatment agent 320 of a Fc effector domain was used to provide a marker for an induced immune response.

In a row 706, an example is illustrated from Kaplan et al., "VEGFR1-positive haematopoietic bone marrow progenitors initiate the pre-metastatic niche," Nature, vol. 438, no.

4, pp. 820-827 (December 2005), which is hereby incorporated by reference and which may be referred to herein as the Kaplan reference. In the Kaplan reference, metastasis is described as a process in which tumor cells mobilize bone-marrow cells to form a site or "pre-metastatic niche" at particular regions (distant from the primary tumor itself), at which the subsequent metastasis may then develop. More specifically, Kaplan describes the idea that cells of a tumor may secrete a molecular/humoral factor(s) that mobilizes bone marrow cells and stimulates fibroblast cells at a distant (future metastatic) site, thereby upregulating fibronectin (a binding, tissue-promoting protein) that serves as a "docking site" for the bone marrow cells. Some of the bone marrow cells were positive for proteins characteristic of haematopoietic progenitor cells, including, for example, vascular endothelial growth factor receptor 1 (VEGFR1), which, in turn, is described as promoting attachment and motility of tumor cells, thereby leading to metastasis. For example, protease production associated with the bone marrow cells may lead to growth factors (e.g., vascular endothelial growth factor (VEGF) that support the developing niche, through, e.g., angiogenesis). In other words, the VEGFR1-positive bone marrow cells serve to form the "pre-metastatic niche" by colonizing a site distant from the tumor, so that subsequently-arriving tumor cells find a hospitable environment at such a site.

Thus, in the example of the row 706, the direct end target 306 may include one or more metastatic and/or pre-metastatic niches or sites that are distant from a primary tumor. For example, such niches may be present in the lungs when the primary tumor includes a melanoma. Then, the discriminated end target 308 may include tissues other than these metastatic niches. The direct intermediate target 310 may include endothelial cells at the metastatic niches, while the discriminated intermediate target 312 may include endothelial cells at other locations. Additionally and/or alternatively, the direct intermediate target 310 may include endothelial cellular structures at the metastatic or pre-metastatic niches, while the discriminated intermediate target 312 may include endothelial cellular structures at other locations. In the example of the row 706, the target-related tissue ancestry correlated binding site 314 includes VEGFR1, which, as referenced above, includes a receptor protein on the endothelial cells (to which VEGF may bind). In this case, and as referenced in the Kaplan reference, the target-related tissue ancestry correlated binding agent 316 may include an antibody to VEGFR1, so that the treatment agent delivery mechanism relative to the target-related tissue ancestry correlated binding agent 318 includes an essentially direct delivery of this antibody, where the antibody to VEGFR1 thereby serves as the treatment agent 320 by blocking the VEGFR1 and preventing formation of, occupying, and/or blocking subsequent interactions with development of the pre-metastatic niche. Of course, the row 706 includes merely one example of target-related tissue ancestry correlated binding site(s) and/or target-related tissue ancestry correlated binding agent(s) that may be located within, or in association with, the pre-metastatic niche(s), where appropriate discovery and/or targeting thereof may be performed by any of the techniques described herein, or other techniques. Moreover, it should be understood from the above description that such target-related tissue ancestry correlated binding site(s) and/or target-related tissue ancestry correlated binding agent(s) may be time-dependent, e.g., with respect to formation and metastasis of the primary tumor. Accordingly, application of the just-referenced techniques may be determined and/or occur based on such time-dependencies, e.g., by applying the techniques for patients at high risk of metastatic disease, but for whom metastatic disease has not yet actualized in the form of established metastases.

In other, related, examples, the treatment(s) just described (i.e., use of an antibody to VEGFR1) should be understood to represent merely an example(s) of how to reduce or eliminate development of the pre-metastatic niche(s) and/or metastasis of the primary tumor. For example, molecular addressing as described herein may be used to slow or stop the upregulation of fibronectin. In such examples, and considering the time-dependent nature of metastasis and treatment just referenced, the alternative treatment modalities (e.g., regulating a presence or development of VEGFR1 and fibronectin) may be seen as complementary to one another. For example, such treatment modalities may be implemented cyclically for the patient 106, the better to disrupt the pre-metastatic/metastatic pathway as a whole, and thereby to increase an efficacy of the overall treatment of the patient 106. Of course, similar comments apply to treatment modalities applied at other points in the pathway, as well as to other pathways, as would be apparent.

Figure 8:
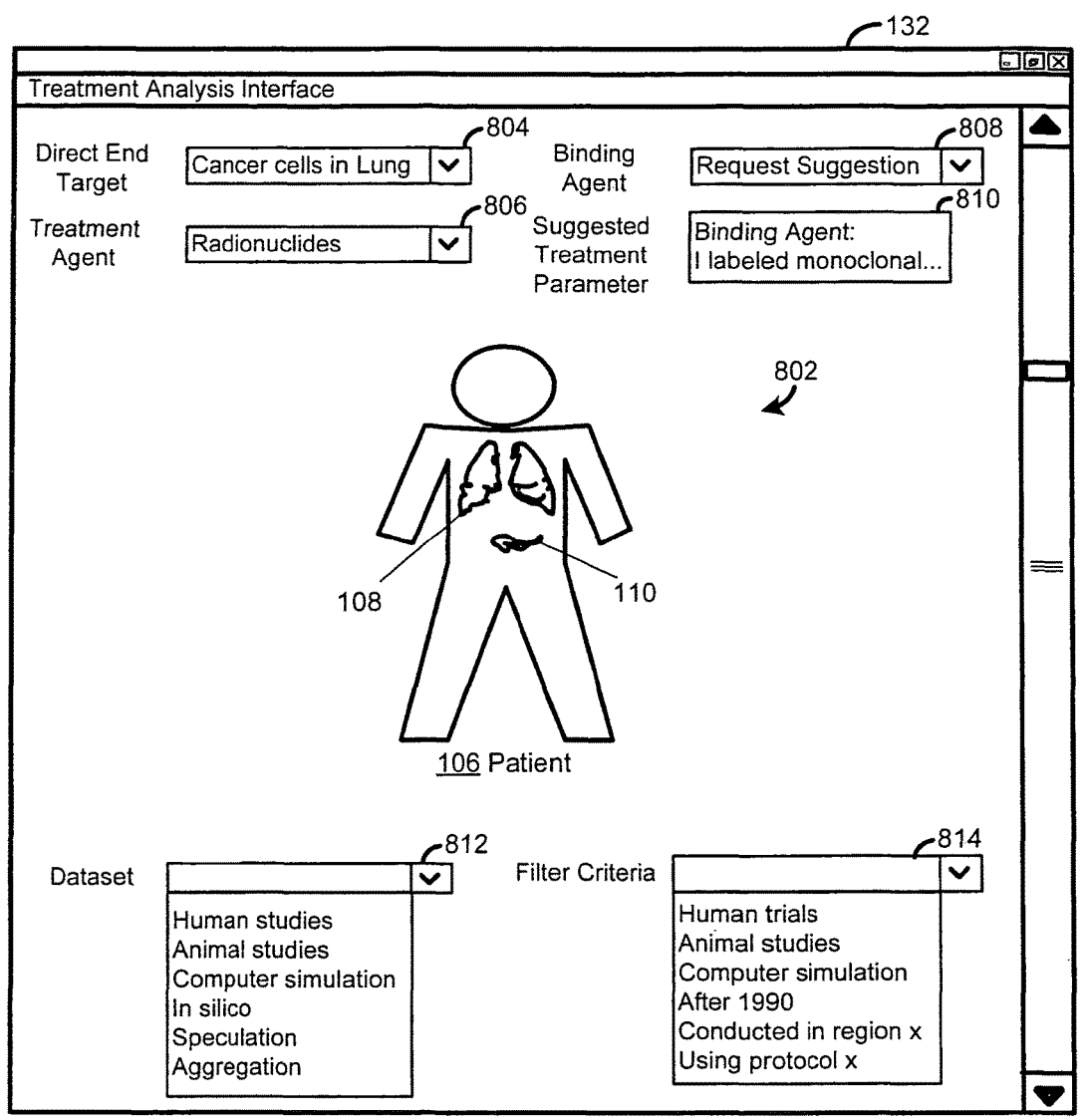
FIG. 8 illustrates an example screenshot of a graphical user interface for accessing predictive data.

FIG. 8 illustrates an example screenshot of a graphical user interface for accessing predictive data. In FIG. 8, an example of the user interface 132 of FIG. 1 is illustrated as providing a graphical illustration 802 of the patient 106. For example, the graphical illustration 802 may include an image of some or all of the patient 106, where the image may include various colors, highlights, or other visual indicators designed to provide information regarding the patient 106, or regarding a diagnosis or treatment of the patient 106. The graphical illustration 802 may illustrate internal organs of interest, and surrounding or related body portions, with varying (and variable) levels of resolution. For example, user controls (not shown in FIG. 8) may be provided that allow the clinician 104 to view the graphical illustration 802 by zooming in or out, or by moving a viewing focus of/on the graphical illustration 802. Although illustrated in FIG. 8 as an outline, the graphical illustration 802 may include other visual representations of the patient 106, which may be generic to a class of patient or specific to a particular patient, and which may include a photograph or other illustration derived from image sensor(s), or a three-dimensional representation of the patient 106. Additionally, or alternatively, the graphical illustration 802 may include a chart, graph, diagram, table, or other representation of data that may be useful to the clinician 104 in diagnosing or treating the patient 106.

In the example of FIG. 8, the user interface 132 includes a plurality of fields 804, 806, 808, 810, 812, and 814. In some implementations, the fields 804-814 allow the clinician to access, analyze, or otherwise consider or use the treatment data 126 of FIG. 1 to diagnose and/or treat the patient 106. For example, as referenced herein, the clinician 104 may determine or consider treatment techniques to select and deliver an appropriate type and/or level of a treatment agent, with an appropriate degree of accuracy, to a desired (direct) end target, while minimizing a negative impact of such a selection/delivery, if any, on other regions of the body of the patient 106. In some implementations, the user interface 132 thus provides the clinician 104 with bases for speculation or conjecture regarding a potential course of treatment or research that may be undertaken with regard to the patient 106. In other words, for example, the user interface 132 allows the clinician 104 to hypothesize about an efficacy, risk, unwanted impact, or side effect of a particular course of treatment that may be undertaken.

For example, the field 804 may include a drop-down menu by which the clinician 104 may select a direct end target that is desired for treatment or analysis. In the example of FIG. 8, the field 804 is illustrated as showing a selection of "cancer cells in lung" as the direct end target. Meanwhile, the field 806 illustrates a selection of "radionuclides" as a potential treatment agent.

As described herein, delivery of radionuclides or other appropriate treatment agents to a desired bodily location may be accomplished by using a "molecular address" provided by a target-related tissue ancestry-correlated binding site, e.g., by associating the treatment agent (radionuclides) with a target-related tissue ancestry-correlated binding agent that is known to deliver the treatment agent to the target-related tissue ancestry-correlated binding site (and thereby, for example, to surrounding target tissue), while discriminating against, or avoiding, ancillary or undesired delivery of the treatment agent to non-target tissue(s). Thus, in the example of FIG. 8, once the clinician 104 selects a desired direct end target using the field 804, and a desired treatment agent in the field 806, then the clinician 104 may select "request suggestion" in the field 808 associated with a target-related tissue ancestry-correlated binding agent, as shown. In this case, the system 100 or similar system (e.g., the system 900 of FIG. 9, discussed in more detail, below) may thus provide a suggestion for the target-related tissue ancestry-correlated binding agent of "I labeled monoclonal antibodies" in the field 810, for consideration and possible use by the clinician 104 in applying the treatment agent (radionuclides) of the field 806 of the direct end target (cancer cells in lung) of the field 804.

Of course, FIG. 8 and the above discussion provide merely a few examples of how the user interface 132 may be used in conjunction with the treatment logic 128 of the treatment system 102 to access the treatment data 126. In other examples, the clinician 104 may request a suggestion for the direct end target in the field 804, or may request a suggestion for the treatment agent 806, or, on the other hand, may simply specify all desired treatment parameters (in which case no suggested treatment parameter need be provided in the field 810). Further, although FIG. 8 is illustrated for the sake of example as including fields for the direct end target, the treatment agent, and the target-related tissue ancestry-correlated binding agent, it should be understood that any of the various treatment parameters mentioned herein, or other treatment parameters, may be selected or provided in conjunction with the user interface 132.

However the treatment parameter(s) are selected and/or provided in the user interface 132, the graphical illustration 802 may be used to provide possible outcomes of a use of the treatment parameter(s) with respect to one or more body portions. For example, in the illustrated example of FIG. 8, where the treatment parameters of the fields 804-810 are selected or provided, the graphical illustration 802 may be used to illustrate a possible outcome of the use of the treatment parameters with respect to the lungs 108 and/or the pancreas 110. For example, since cancer cells in the lungs 108 are intended to be used as the direct end target, as specified in the field 804, the graphical illustration 802 may be used to illustrate an effect of delivering the specified treatment agent (radionuclides) of the field 806 to the lungs 108, using the target-related tissue ancestry-correlated binding agent suggested in the field 810 (also using, it will be appreciated, the appropriate target-related tissue ancestry-correlated binding site associated with the lungs 108 to which the target-related tissue ancestry-correlated binding agent is known to bind). For example, a color scheme or other visual indicator(s) may be used to indicate an efficacy of the specified treatment parameters with respect to the lungs 108, e.g., by providing the illustration of the lungs 108 in different colors to indicate the efficacy of the specified treatment parameters. Of course, other audio or visual indicators may be used, e.g., the graphical illustration 802 may include a brightness or other visual aspect of the illustration of the lungs 108 that is varied in direct or indirect correspondence with an efficacy of the specified treatment parameters.

As a result, the clinician 104 may, for example, observe and judge an efficacy of a plurality of successively-specified treatment parameters, simply by selecting or requesting examples and combinations thereof, using the fields 804-810. By use in part of such visual indicators as those just described, the clinician 104 may quickly and easily make judgments about which treatment parameter(s) may be most useful in a given diagnostic, treatment, or research scenario.

In some implementations, the graphical illustration 802 may be used to provide other possible outcomes of the use of the treatment parameter(s), beyond illustrating an efficacy thereof. For example, the graphical illustration 802 may automatically illustrate side effects, unwanted impacts, or other risks, ambiguities or consequences of using the specified treatment parameter(s). For example, as described herein, it may be the case that use of the specified treatment parameter(s) may result in an undesired side effect of, for example, delivery of the treatment agent (e.g., radionuclides) to other body portions. Accordingly, the graphical illustration 802 may illustrate body portions that may be affected by the use of the treatment parameter(s) in an undesired, unwanted, and/or detrimental manner. For example, the graphical illustration 802 may include a representation of the pancreas 110, which may be affected by the treatment agent (radionuclides) in an undesired manner. Again, visual indicators may be used to indicate a nature and/or extent of the undesired effect, using, e.g., a designated color scheme, highlighting, numerical or graphical representation, or other visual indications.

Thus, again, the clinician 104 may gain useful information for diagnosing or treating the patient 106, or for general research/inquiry into uses of different treatment parameters. For example, by specifying different (combinations of) treatment parameters, the clinician may observe an efficacy of a desired treatment, relative to a nature and extent of unwanted impacts thereof. For example, the clinician 104 may be reminded (or made aware) of certain side effects that may not otherwise have been considered or known, and may respond accordingly. For example, if the patient 106 is known to have a weakened or somewhat dysfunctional pancreas, then different treatment parameters may be selected to find combinations thereof that retain a desired level of efficacy, while avoiding dangerous or unwanted application of the treatment agent to the pancreas 110.

In providing the graphical illustration 802, including possible outcomes (both beneficial and detrimental) of the use of the specified treatment parameters, the user interface 132 may access and use the treatment data 126, using the treatment logic 128. In the example of FIG. 8, the treatment data 126 may include a plurality of datasets used by the treatment logic 128 to provide the graphical illustration 802, where each dataset may be associated with at least one predictive basis for providing the possible outcome(s) of the use of the various treatment parameters.

For example, a first such dataset may be associated with a first predictive basis that may include previous studies or trials performed on human subjects. That is, results of previous studies or trials performed on human subjects may be stored in the first dataset, and these results may be tagged, identified, or otherwise characterized within the treatment data 126 as having a certain type or degree of predictive value. For example, the first dataset may be characterized as being more predictively useful than results from a second dataset associated with studies or trials based on animals, simply by virtue of having been performed on human subjects. In other examples, the results in the first dataset may be characterized as having been performed in a certain timeframe or environment, under certain funding and/or procedural guidelines, within a defined area or type of medical practice, or having some other predictive basis and/or value. In these and other such examples, the first dataset may be designated to have more or less predictive value than a second dataset that also stores results of studies or trials performed on human subjects, but where the identified characteristic(s) is different in quantity or quality (e.g., performed in a different timeframe or environment, or under more or less stringent funding and/or procedural guidelines, or in a different area of medical practice (e.g., holistic/alternative as compared to traditional)).

In the example of FIG. 8, a field 812 is included that allows the clinician 104 to specify one or more datasets to be used by the treatment logic 128 in generating the graphical illustration 802. For example, the field 812 illustrates that the clinician 104 may select one or more datasets associated with human studies, animal studies, computer simulations. "in silico" datasets, speculated datasets, or aggregated datasets (where, for example, the clinician 104 may specify different combinations or aggregations of the different datasets, e.g., by selecting multiple ones of the listed examples). Of course, these are just examples, and any other knowledge source may be used, as would be apparent, including, for example, any type of in vivo or in vitro or in silico study.

In this way, for example, the clinician 104 may use the user interface 132 as a convenient tool to perform analysis, speculation, or prediction of a possible outcome of the use of specified treatment parameters, based on the different datasets having different predictive bases. For example, for the treatment parameters specified in the fields 804-810, the clinician may first select "human studies" in the field 812, whereupon the user interface 132 may provide the graphical illustration 802 with a first illustration of the lungs 108, perhaps in association with a certain color or other visual indicator designed to illustrate an efficacy of the treatment parameters with respect to the lungs 108 (or, more specifically, with respect to certain types of cancer cells within the lungs 108). In this first example, the pancreas 110 may not initially be illustrated (or may be illustrated but not visually marked or altered), since, for example, the human studies providing the first predictive basis of the first dataset may not have shown any adverse effects with respect to the pancreas 110.

Then, the clinician may specify a second dataset having a second predictive basis, such as, for example, a dataset associated with "animal studies," as selected from the field 812. In this case, the user interface 132 may modify the graphical illustration 802 to provide a modified graphical illustration that includes the pancreas 110 (and/or a visual indicator associated therewith), and that thereby illustrates that the results of the second dataset indicate that a possible outcome of the use of the specified treatment parameters includes unwanted application of the treatment agent to the pancreas 110.

As a result, for example, the clinician 104 may make a more informed decision about a future course of action regarding a diagnosis or treatment of the patient 106. For example, the fact that the animal studies of the second dataset indicate the possible outcome of unwanted impact on the pancreas 110 may not be considered to be conclusive with regard to predicting the same or similar effect on the patient 106 (assuming that the patient 106 is human in this example). Nonetheless, for example, the clinician 104 may be reminded of a possible side effect or other concern that may otherwise have been discounted or forgotten, or, as another example, where the clinician 104 knows that the patient 106 has a weakened or dysfunctional pancreas, the above-described information provided by the user interface 132 may be sufficient for the clinician 104 to continue specifying different treatment parameters in the fields 804-810, in an attempt to determine a more appropriate treatment for the patient 106.

Similar comments apply regarding an efficacy of specified treatment parameter(s) with regard to the lungs 108. For example, the first dataset associated with the human studies may indicate a certain degree of efficacy of the specified treatment parameters of the fields 804-810 (e.g., by way of an appropriate visual indicator, such as color), while the second dataset associated with the animal studies may indicate a greater (or lesser) degree of efficacy. In this case, the clinician 104 may select the specified treatment parameters for use with the patient 106, as compared to alternate treatment parameters. That is, where the clinician 104 is choosing between two or more possible courses of treatment, the clinician 104 may arrive at a selection of a treatment based on a consideration of possible outcomes illustrated by the user interface 132, based on different ones of the datasets of the field 812.

In addition to diagnosis and treatment of the patient 106, the user interface 132 may be used, for example, as a research or speculation tool for determining and assessing possible future treatments. For example, the clinician 104 may be in the process of determining a future course of research with respect to different (combinations of) treatment parameters. In deciding between the different courses of research that may be taken, the clinician 104 may consider possible outcomes of the treatment parameters, using the various datasets of the field 812. For example, if a particular combination of treatment parameters shows a high degree of efficacy (and/or a low degree of unwanted side effects) based on multiple ones of the datasets of the field 812, then the clinician 104 may consider that the particular combination merits further research or clinical-use consideration.

Further in FIG. 8, a field 814 allows the clinician 104 to apply a filter criteria to the dataset(s) specified in the field 812. For example, the filter criteria may remove portions of the current dataset(s) that the clinician 104 may feel have less predictive value in determining the possible outcome(s) of using the specified treatment parameters. For example, the clinician may begin consideration of possible outcomes of the specified treatment parameters by selecting "aggregation" in the field 812, so that the graphical illustration 802 illustrates the possible outcome of use of the treatment parameters based on all of the datasets of the field 812. Then, the clinician 104 may selectively remove a contribution of a selected one or more of the datasets, by, for example, selecting a dataset associated with "animal studies" in the field 814, or selecting a filter criteria of "computer simulation(s)" to remove computer-simulated results from the combined datasets.

In other examples, the filter criteria may not correspond directly or in a one-to-one relationship with one of the datasets of the field 812. For example, the filter criteria may filter information from a combination of datasets, i.e., information that is common to each of the datasets. For example, if the clinician 104 selects "human studies" and "animal studies" using the field 812, then the clinician 104 may select "after 1990" in the field 814 to remove all results from both datasets that were collected prior to 1990. Similarly, as shown in FIG. 8, the field 814 may be used to filter results from one or more datasets based on whether the results were obtained in a particular geographical region (i.e., "region x"), or were obtained in studies conducted according to a particular protocol (i.e., "protocol x").

Thus, FIG. 8 illustrates an example of a graphical user interface including at least a first portion (e.g., one or more of the fields 804-814) configured to receive a first request to provide a graphical illustration (e.g., the graphical illustration 802) of a first possible outcome of a use of a treatment parameter with respect to at least one body portion (e.g., the lungs 108 and/or the pancreas 110), based on at least one first dataset associated with at least one predictive basis (e.g., the first dataset/first predictive basis selected using the field 812). FIG. 8 further illustrates that such a graphical user interface may include at least a second portion (e.g., one or more of the fields 804-814) configured to receive a second request to apply a filter criteria to the at least one dataset to provide a modified graphical illustration (e.g., a modified version of the graphical illustration 802) of a second possible outcome of the use of the treatment parameter. Thus, the graphical user interface also may include a third portion configured to illustrate the graphical illustration and the modified graphical illustration (e.g., the portion of the user interface 132 of FIG. 8 including the graphical illustration 802), so as, for example, to include at least a portion of the at least one body portion (e.g., at least a portion of the lungs 108), and/or to include one other body portion (e.g., the pancreas 110) in addition to the at least one body portion (e.g., the lungs 108).

Figure 9:
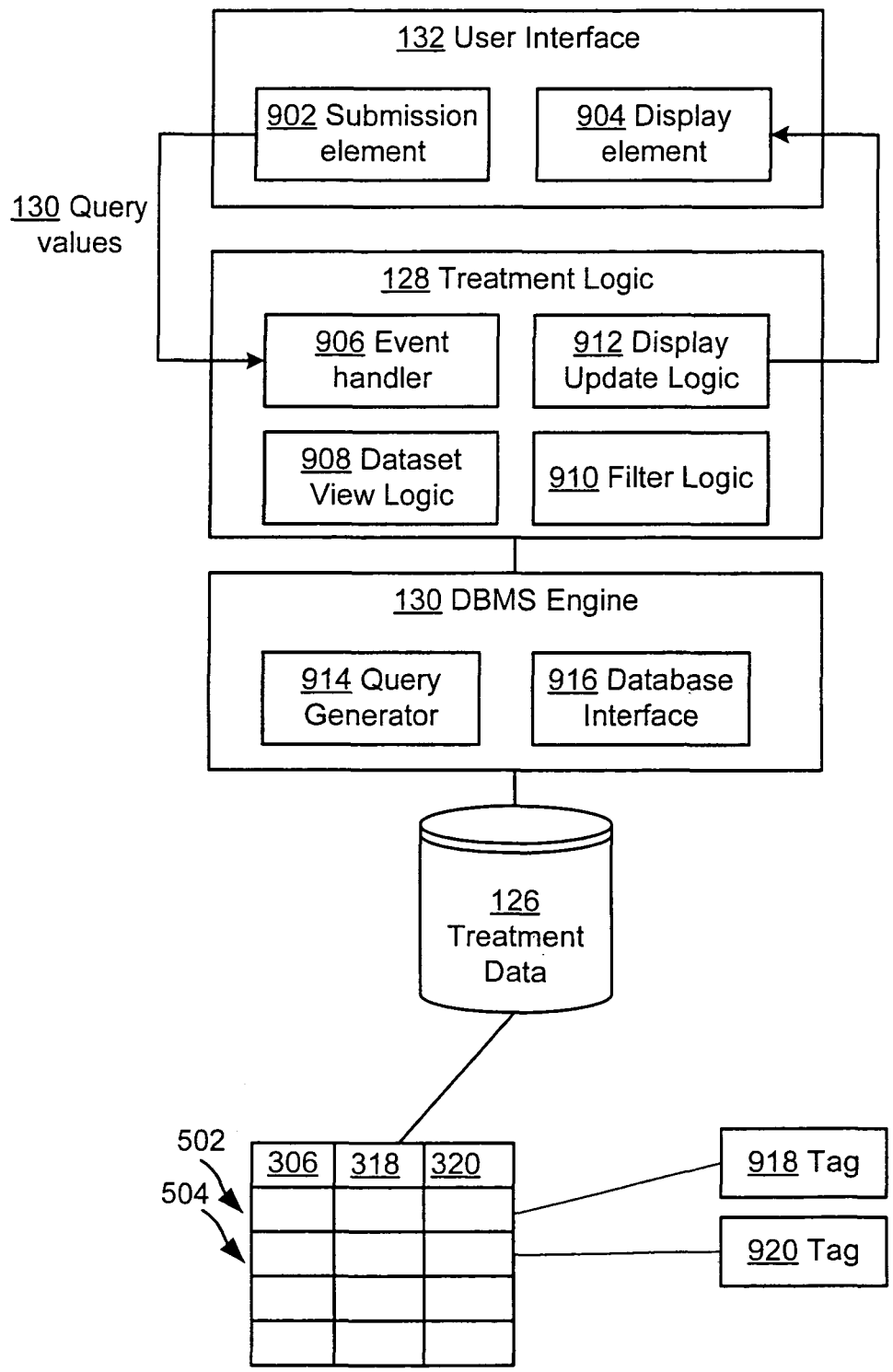
FIG. 9 illustrates an alternative embodiment of the clinical system of FIG. 1 in which the clinical system is configured to provide access to predictive data.

FIG. 9 illustrates an alternative embodiment of the clinical system of FIG. 1 in which the clinical system is configured to provide access to predictive data. Thus, FIG. 9 illustrates examples by which the user interface 132 may be used to access or otherwise interact with the treatment data 126, in order to provide, for example, the various features, functionalities, and effects described above with respect to FIG. 8.

In the example of FIG. 9, the user interface 132 is illustrated as containing generic elements 902 and 904, i.e., a submission element 902 and a display element 904. Generally, the submission element 902 may include any icon, button, field, menu, or box that may be used by the clinician 104 to select, submit, or request information. The display element 904 may include any element of the user interface 132 used to provide information to the clinician 104, where it should be understood that in some cases the submission element 902 and the display element 904 may include the same element, or related elements, since the clinician 104 may enter or select data using a given element and then may view the results of the entry or selection using the same element. Thus, and as should be apparent from FIG. 8, the submission element 902 may include, for example, any of the fields 804, 806, 808, 812, or 814, since the clinician 104 may submit treatment parameters, datasets, and/or filter criteria therewith. Meanwhile, any of the fields 804-814 may be considered to be an example of the display element 904, since any of these may be used to display information (e.g., a result of a selection of a treatment parameter, dataset, or filter criteria). Of course, the graphical illustration 802 is another example of the display element 904.

Thus, for example and as described herein, the clinician 104 may utilize the submission element(s) 902 to select the treatment parameters (or to request a suggestion of one or more treatment parameters), or to specify one or more datasets to be used in providing the possible outcome(s) of using the treatment parameters, or to specify a filter criteria to be used in filtering the dataset(s). For example, when the clinician 104 uses the field 812 to select the dataset "human studies," then this submission is passed to the treatment logic 128, or, more specifically, is passed to an event handler 906 that receives the submission and performs an initial classification, logging, routing, or other handling of the type and value of the submission event, e.g., here, the type including a specification of a dataset to be used and the value including the selected dataset "human studies."

For example, a submission event associated with a use of the submission element 902 by the clinician 104 may be passed by the event handler 906 either to dataset view logic 908 and/or filter logic 910. As described in more detail herein, the dataset view logic 908 and the filter logic 910 represent aspects of the treatment logic 128 associated with analyzing specified treatment parameters with respect to specific portions (e.g., datasets) of the treatment data 126, so as, for example, to provide the uses and effects described above with respect to the graphical illustration 802, e.g., by using display update logic 912 to update the display element(s) 904.

More specifically, for example, the dataset view logic 908 may be used to analyze a submission event from the event handler 906 and determine, for example, that the clinician 104 has selected both "human studies" and "animal studies" using the field 812. The dataset view logic 908 may then interact with a query generator 914 of the DBMS engine 130 to generate a query that may be passed by a database interface 916 to the treatment data 126. In this case, it also may occur that the event handler 906 may pass a second submission event (which may occur concurrently or in a sequence), in which the clinician 104 selects "before 1990" as a filter criteria in the field 814, to the filter logic 910. Thus, the event handler 906 is responsible for correlating the two submission events, so that the filter logic 910 may correspond the specified filter criteria against the (in this case, two) datasets specified to the dataset view logic 908.

In these and other examples, then, the treatment logic 128 may interact with the DBMS engine 130 to construct a query and pass the query to the treatment data 126. For instance, in the example just given, a query may be built that includes a Boolean combination of a first dataset associated with "human studies" AND a second dataset associated with "animal studies," where the query is generated with a form and structure that is appropriate for the treatment data 126 (e.g., using the Structured Query Language (SQL) in a case where the treatment data 126 implements a relational database).

In FIG. 9, example data results and/or datasets are referenced to FIG. 5, where, as shown in FIG. 5, rows 502 and 504 include (abbreviated) data results for a direct end target 306, a target-related, tissue ancestry-correlated binding agent 316, and a treatment agent 320. In this case, for example, data from the row 502 may be associated with a tag 918 indicating that data from the row 502 is associated with human studies and should therefore be included in a first dataset, while data from the row 504 may be associated with a tag 920 indicating that data from the row 504 is associated with animal studies and should therefore be included in a second dataset (where such examples are intended to illustrate a use of the tags 918, 920 with respect to a query from the DBMS engine 130, and are not intended, necessarily, with specific reference to the Oh reference of FIG. 5). In some implementations, for example, the tags 918 and 920 may be associated with use of the eXtensible Markup Language (XML) in constructing the treatment data 126, where use of XML or other semi-structured databases is discussed in more detail, herein. In this case, then, the database interface 916 may include an XML interface.

It should be understood, then, that the tags 918, 920 may be used in generating and executing queries against the treatment data 126 by either the dataset view logic 908 or the filter logic 910. For example, the filter logic 910 may interact with the query generator 914 to generate a query against the treatment data 126 (or against a result set of a query generated in conjunction with the dataset view logic 908), using the tags 918, 920 to identify, and thereby remove/exclude, data that matches the filter criteria from a corresponding result set.

Once an appropriate result set(s) has been generated by the dataset view logic 908 and/or the filter logic 910, the display update logic 912 may be used to update the display element 904 appropriately, as referenced herein. For example, the display update logic 912 may include logic for implementing the color schemes mentioned above, or for providing any other visual indicator(s) that may be used to convey information in association with the graphical illustration 802.

Figure 10:
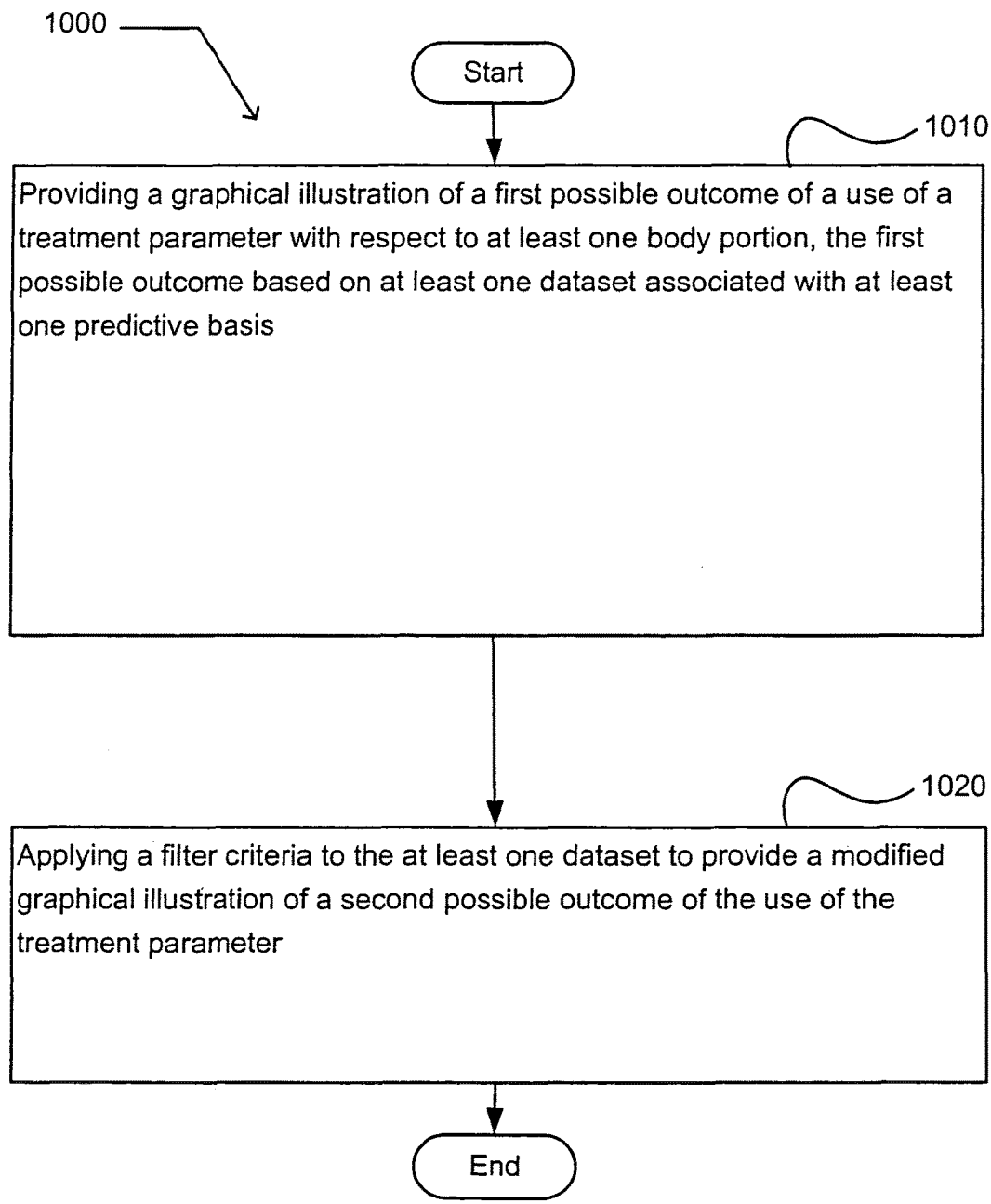
FIG. 10 illustrates an operational flow representing example operations related to accessing predictive data.

FIG. 10 illustrates an operational flow representing example operations related to accessing predictive data. In FIG. 10 and in following figures that include various examples of operational flows, discussion and explanation may be provided with respect to the above-described examples of FIGS. 1-9, and/or with respect to other examples and contexts. However, it should be understood that the operational flows may be executed in a number of other environments and contexts, and/or in modified versions of FIGS. 1-9. Also, although the various operational flows are presented in the sequence(s) illustrated, it should be understood that the various operations may be performed in other orders than those which are illustrated, or may be performed concurrently.

After a start operation, the operational flow 1000 moves to a providing operation 1010 where a graphical illustration of a first possible outcome of a use of a treatment parameter with respect to at least one body portion is provided, the first possible outcome based on at least one dataset associated with at least one predictive basis. For example, as shown in FIG. 8, the graphical illustration 802 may be provided using the user interface 132, where the graphical illustration 802 may provide a first possible outcome of a use of one or more of the treatment parameters of the fields 804-810 of FIG. 8. As described herein, the first possible outcome may be based on at least one dataset that may be specified, for example, using the field 812 (e.g., by a selection of the clinician 104 of all datasets of the field 812, by selecting the "aggregation" option of the field 812), where the at least one predictive basis corresponds to the at least one dataset and may be pre-configured, defined, or characterized (e.g., as being either relatively more or less predictively useful than a comparison dataset). Although the graphical illustration 802 includes specific body portions such as the lungs 108 and pancreas 110, it should be understood that the graphical illustration 802 may be provided with respect to an entire body of the patient 106 (e.g., where the treatment parameter includes a blood pressure or other characteristic of the patient 106 that is not localized to a particular body portion), and may be provided as an additional or alternative representation of data (e.g., as a blood pressure chart illustrated along with, or as some or all of, the graphical illustration 802).

Then, in an applying operation 1020, a filter criteria may be applied to the at least one dataset to provide a modified graphical illustration of a second possible outcome of the use of the treatment parameter. For example, the graphical illustration 802 of FIG. 8 may be modified to obtain the modified graphical illustration, in response to a subsequent selection by the clinician 104 of a filter criteria (e.g., by selecting "animal studies" in the field 814). Accordingly, the graphical illustration 802 may be modified to remove any portion thereof that is related to, or based on, the "animal studies" dataset of the field 812. In this sense, it should be understood that the applying of the filter criteria may occur by altering the graphical illustration 802 or some part thereof, including new or additional aspects of the graphical illustration 802, or replacing some or all of the graphical illustration 802, e.g., in conjunction with any of the techniques described above with respect to the providing operation 1010, or with other techniques, including the use of visual indicators and/or illustrated/highlighted body portions. As a result of the operations 1010 and 1020, for example, the clinician 104 may view the first possible outcome as predicted using the combined predictive bases of all the datasets of the field 812, and as illustrated in the graphical illustration 802. The clinician 104 may subsequently view the second possible outcome as predicted using all of the above-described combined predictive bases, but with an effect of the predictive basis associated with the "animal studies" dataset having been removed for illustration of the modified version of the graphical illustration 802.

In this regard, it should be understood that the providing operation 1010 and/or the applying operation 1020 may be performed with respect to a digital representation (e.g., as digital data), for example, of the treatment parameter, the dataset(s), and/or the filter criteria. For example, as may be understood with reference to FIG. 9, the treatment logic 128 may accept a digital or analog (for conversion into digital) representation of the at least one treatment parameter from the user interface 132 (e.g., from the submission element 902), for presentation to the DBMS engine 130 and/or the treatment data 126. As another example, the treatment logic 128 may provide a digitally-encoded representation of the graphical illustration 802, or a modified version thereof, based on the treatment data 126, where the treatment data 126 may be implemented and accessed locally, and/or may be implemented and accessed remotely.

Thus, an operation(s) may be performed related either to a local or remote storage of the digital data, or to another type of transmission of the digital data. As discussed herein, in addition to accessing, querying, recalling, or otherwise obtaining the digital data for the providing operation, operations may be performed related to storing, assigning, associating, or otherwise archiving the digital data to a memory, including, for example, sending and/or receiving a transmission of the digital data from a remote memory. Accordingly, any such operation(s) may involve elements including at least an operator (e.g., either human or computer) directing the operation, a transmitting computer, and/or a receiving computer, and should be understood to occur within the United States as long as at least one of these elements resides in the United States.

Figure 11:
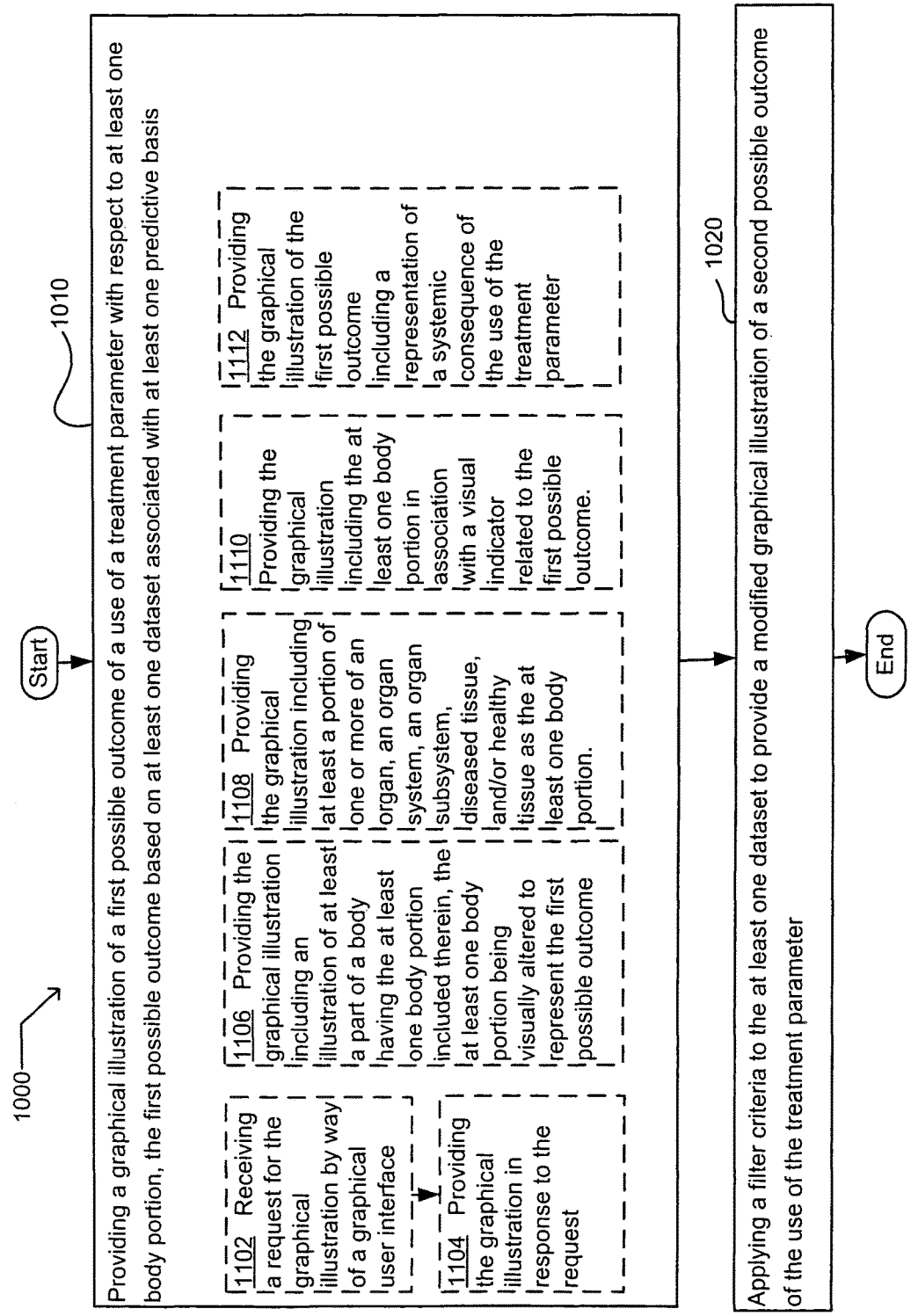
FIG. 11 illustrates an alternative embodiment of the example operational flow of FIG. 10.

FIG. 11 illustrates alternative embodiments of the example operational flow 1000 of FIG. 10. FIG. 11 illustrates example embodiments where the providing operation 1010 may include at least one additional operation. Additional operations may include operation 1102, operation 1104, operation 1106, operation 1108, operation 1110, and/or operation 1112.

At the operation 1102, a request for the graphical illustration is received by way of a graphical user interface. For example, a request from the clinician 104 may be received for the graphical illustration 802, using the user interface 132. Then, at the operation 1104, the graphical illustration may be provided in response to the request. For example, and continuing the example just given, the graphical illustration 802 may be provided in response to the request of the clinician 104.

At an operation 1106, the graphical illustration including an illustration of at least a part of a body having the at least one body portion included therein may be provided, the at least one body portion being visually altered to represent the first possible outcome. For example, as shown in FIG. 8, the graphical illustration 802 may be provided with the at least a part of a body having the at least one body portion (e.g., the lungs 108) included therein. Further, and as referenced herein, the at least one body portion (e.g., the lungs 108) may be visually altered with respect to a remainder of the graphical illustration 802, e.g., the lungs 108 may be highlighted, identified, altered in color or intensity or appearance, caused to flash at a certain repetition-frequency, or otherwise be visually marked for notification to the clinician 104.

At an operation 1108, the graphical illustration may be provided including at least a portion of one or more of an organ, an organ system, an organ subsystem, diseased tissue, and/or healthy tissue as the at least one body portion. For example, as illustrated in FIG. 8, the at least one body portion may include the lungs 108 and/or the pancreas 110.

At an operation 1110, the graphical illustration may be provided including the at least one body portion in association with a visual indicator related to the first possible outcome. For example, the graphical illustration 802 of FIG. 8 may be provided including the lungs 108, pancreas 110, or other body portion, where the mere inclusion of such a body portion may be considered to be a visual indicator related to the first possible outcome (e.g., where the pancreas 110 is illustrated only when it is determined by the treatment logic 128 that possible side effects may be associated with the pancreas 110 when using the lungs 108 (or cancerous cells therein) as a direct end target). In other implementations, and as referenced herein, the visual indicator may include a coloring, highlighting, designating, marking, identifying, shading, cross-hatching, flashing, or other visual effect. In such examples, the visual indicator(s) may be related to, or indicate, the first possible outcome, e.g., the efficacy (or risks, or unwanted consequences) of one or more (combinations of) treatment parameters. For example, the graphical illustration 802 or appropriate portion(s) thereof may have its color changed, or may be highlighted or otherwise marked/designated to indicate a level of efficacy of selected treatment parameter(s). For example, an efficacy of each treatment parameter may be shown individually or together, since, for example, an efficacy of the target-related, tissue ancestry-correlated binding agent of the field 808 may refer to an ability of such an agent to deliver any treatment agent to (a corresponding target-related, tissue ancestry-correlated binding site within) a direct end target of the field 804, irrespective of which treatment agent is associated therewith. Meanwhile, an efficacy of the treatment agent of the field 806 may refer to an actual treatment result (e.g., reduction or destruction of cancer cells), and, in another example, an efficacy of the combination of treatment parameters may refer to an overall success of the treatment, including management or reduction of associated risks and side effects.

At the operation 1112, the graphical illustration of the first possible outcome is provided including a representation of a systemic consequence of the use of the treatment parameter. For example, as referenced herein, the first possible outcome may include raised/lowered blood pressure, raised/lowered temperature, or other outcomes that are systemic to the patient 106, and which may or may not be displayed in the context of an illustration of a specific organ or other highly-localized body portion. For example, as described with reference to the row 706 of FIG. 7, application of the target-related tissue ancestry correlated binding agent of the field 808 may occur with respect to a number of pre-metastatic niches, which may include very small sites within (or in association with) one or more tissues or organs (e.g., the lungs 108). In such cases, the graphical illustration 802 may include a representation of such systemic consequences, e.g., by visual indicators that are distributed in an appropriate and/or representative fashion within an illustration of a body of the patient 106, or by an ancillary chart, graph, or other representation that may be used to present or describe at least some aspect of the first possible outcome.

Figure 12:
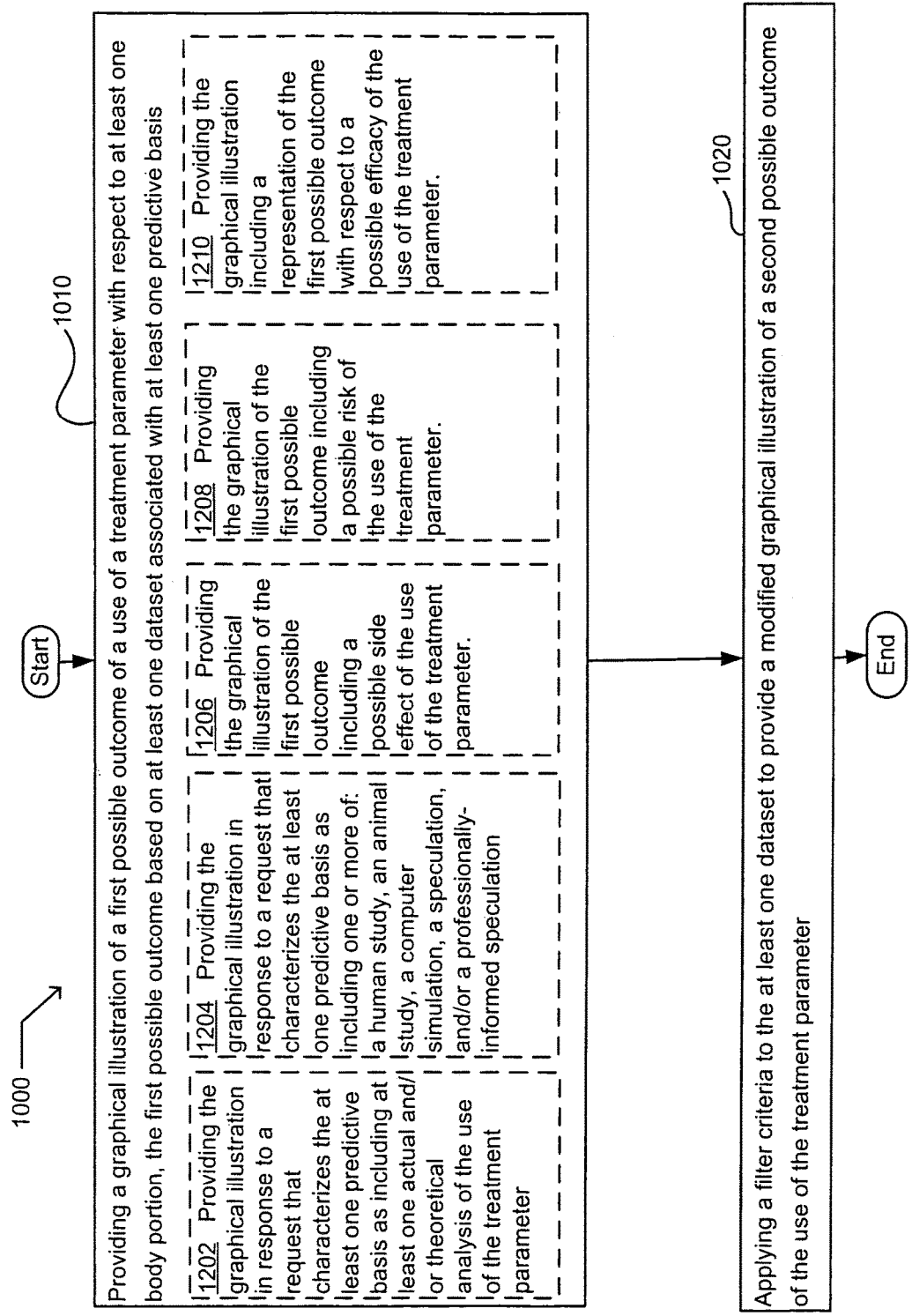
FIG. 12 illustrates an alternative embodiment of the example operational flow of FIG. 10.

FIG. 12 illustrates alternative embodiments of the example operational flow 1000 of FIG. 10. FIG. 12 illustrates example embodiments where the providing operation 1010 may include at least one additional operation. Additional operations may include operation 1202, operation 1204, operation 1206, operation 1208, and/or operation 1210.

At the operation 1202, the graphical illustration may be provided in response to a request that characterizes the at least one predictive basis as including at least one actual and/or theoretical analysis of the use of the treatment parameter. For example, the user interface 132 may receive a request from the clinician 104 through a selection of one of the values of the field 812, where the field 812 may include an actual analysis (e.g., human studies or animal studies, or any in vivo or in vitro study) and/or a theoretical analysis (e.g., in silico and/or computer simulations, or speculation).

At the operation 1204, the graphical illustration may be provided in response to a request that characterizes the at least one predictive basis as including one or more of: a human study, an animal study, a computer simulation, a speculation, and/or a professionally-informed speculation. For example, the user interface 132 may receive the request from the clinician 104 by way of the field 812, where the clinician 104 may use the field 812 to specify human studies, animal studies, or any of the other predictive bases included therein, or other predictive bases that may be provided, or combinations thereof (where it will be appreciated that a human study or animal study (or similar terminology), includes a human-based study or an animal-based study, respectively).

At the operation 1206, the graphical illustration of (e.g., associated with) the first possible outcome may be provided including a possible side effect of the use of the treatment parameter. For example, the graphical illustration 802 may include the pancreas 110, where the pancreas 110 may be affected by the desired treatment for treating the cancer cells in the lungs 108. Similarly, the graphical illustration 802 may include a visual indicator associated with the pancreas 110, where an appearance of the visual indicator 110 (e.g., brightness, color shade, or frequency of flashing) may be indicative of a type or extent of the side effect. In another example, a chart, text box, or other call-out may be included in conjunction with the human body image of the graphical illustration 802, in which the nature or extent of the side effect may be included for review by the clinician 104.

At the operation 1208, the graphical illustration of the first possible outcome may be provided including a possible risk (e.g., a traditional risk and/or ambiguity) of the use of the treatment parameter. For example, the graphical illustration 802 may be provided with corresponding visual indicators, call-outs, or other information designed to inform the clinician 104 of risks associated with one or more of the treatment parameters specified in the fields 804-810. For example, such risks or unwanted impacts may include a risk of lowered efficacy of one or more treatment parameters where certain treatment parameters are used in combination, e.g., where the clinician 104 selects the combination of treatment parameters to avoid certain side effects, at the possible cost of a lowered efficacy of the treatment as a whole.

At the operation 1210, the graphical illustration may be provided including a representation of the first possible outcome with respect to a possible efficacy of the use of the treatment parameter. For example, the user interface 132 may provide the graphical illustration 802 as including a visual illustration of the possible outcome, perhaps including an illustration of a healthy organ (e.g., the lungs 108) to illustrate success of a specified treatment.

Figure 13:
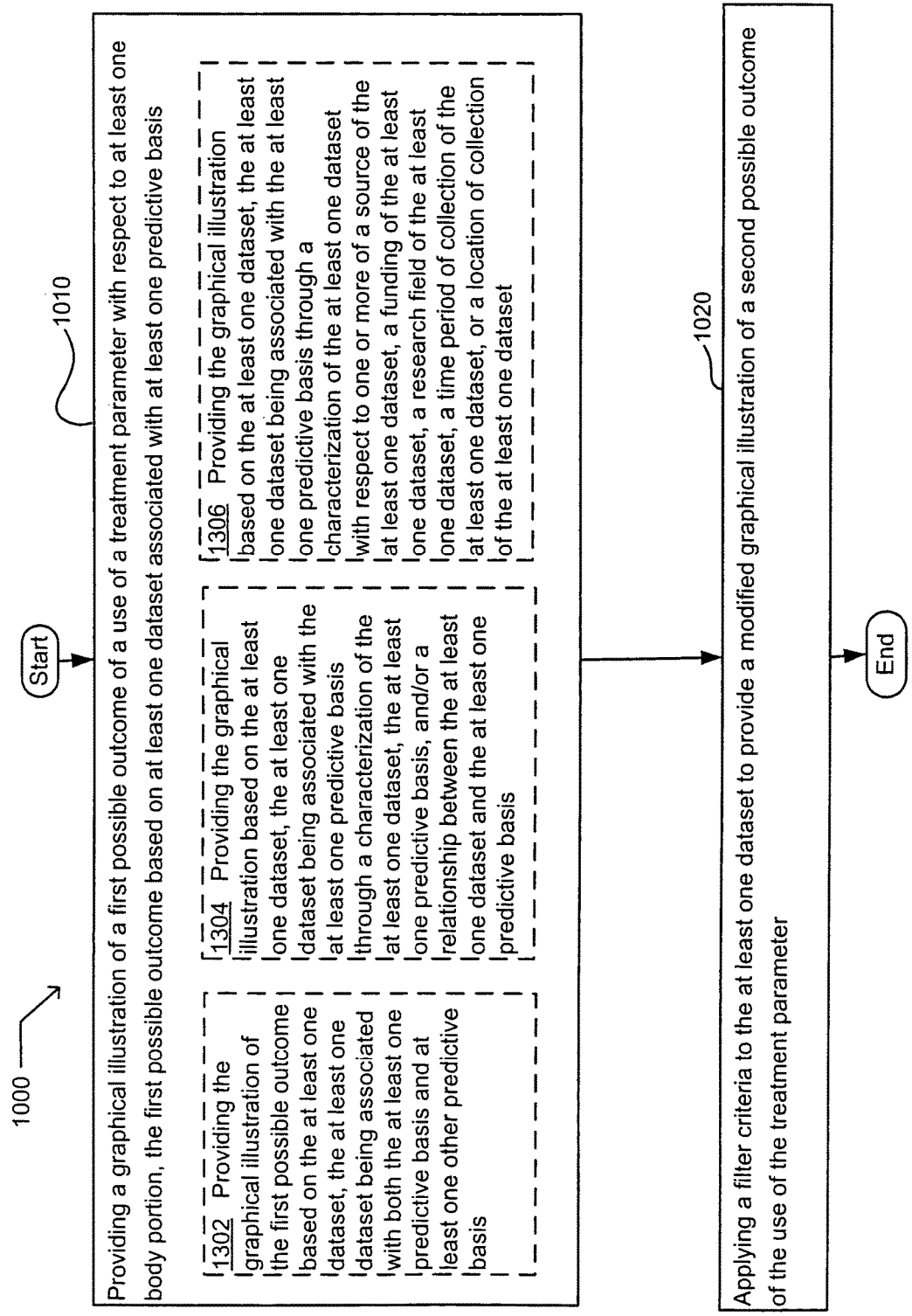
FIG. 13 illustrates an alternative embodiment of the example operational flow of FIG. 10.

FIG. 13 illustrates alternative embodiments of the example operational flow 1000 of FIG. 10. FIG. 13 illustrates example embodiments where the providing operation 1010 may include at least one additional operation. Additional operations may include operation 1302, operation 1304, and/or operation 1306.

At the operation 1302, the graphical illustration of the first possible outcome may be provided based on the at least one dataset, the at least one dataset being associated with both the at least one predictive basis and at least one other predictive basis. For example, the graphical illustration 802 may be provided based on at least one dataset specified in the field 812 as being associated with a first predictive basis, such as "human studies," where results from at least one other dataset may be included in the first dataset having another predictive basis, such as "animal studies." In other words, results from different studies, datasets, and/or predictive bases may be combined to provide the graphical illustration 802, so that, as described herein, the clinician 104 may consider such combinations when deciding on a diagnosis, treatment, or course of research. In this regard, and as described in more detail herein, it should be understood that in many cases, a predictive basis of "human studies" may be assumed to be more predictively useful than a predictive basis of "animal studies" in the context of deciding diagnosis, treatment, or research for human patients. More generally, however, a predictive basis and/or a relative predictive value thereof may be assigned or associated with results, data, or datasets within the treatment data 126, prior to a use of the user interface 132 by the clinician 104, using, e.g., the tags 918 and 920, or similar techniques. That is, in some implementations, different predictive bases may be objectively and verifiably designated as having a defined relative value of predictive usefulness (e.g., relative to one another). Accordingly, one skilled in the art would appreciate that no subjectivity is involved in providing the graphical illustration 802 (as described herein) based on the different predictive bases, as those predictive bases may be provided in associated software, hardware, and/or firmware. Of course, the graphical illustration 802 may nonetheless have more or less subjective value to the clinician 104, based on a personal value or judgment of the clinician 104. In other implementations, an artificial intelligence engine may be used to make semantic decisions regarding assessment(s) of the relative predictive value or usefulness of the different predictive bases.

At the operation 1304, the graphical illustration may be provided based on the at least one dataset, the at least one dataset being associated with the at least one predictive basis through a characterization of the at least one dataset, the at least one predictive basis, and/or a relationship between the at least one dataset and the at least one predictive basis. For example, as just referenced, the graphical illustration 802 may be provided based on at least one dataset that includes "human studies" as specified in the field 812. More generally, different datasets including different human studies, or different types of human studies, may be included, where each such dataset may be characterized as having a certain predictive value with regard to the possible outcome. For example, such a characterization may be implemented through use of the tags 918, 920, or using some other technique for characterizing data within the treatment data 126. Such characterizations may be universal through the treatment data 126, so that, for example, all human studies of a certain type are associated with a first predictive basis or value. In other implementations, such characterizations may be assigned by, or determined for, individual clinicians. For example, different clinicians may assign different predictive values to different (types of) datasets.

At the operation 1306, the graphical illustration may be provided based on the at least one dataset, the at least one dataset being associated with the at least one predictive basis through a characterization of the at least one dataset with respect to one or more of a source of the at least one dataset, a funding of the at least one dataset, a research field of the at least one dataset, a time period of collection of the at least one dataset, or a location of collection of the at least one dataset. For example, the at least one dataset may be characterized by a source of funding of the research that supplied the results of the at least one dataset, where, for example, a certain funding source may be associated with a higher predictive value than others. Similarly, a research field associated with the at least one dataset (e.g., oncology or hematology) may be associated with, or characterized as, having a greater or lesser predictive value, e.g., through use of the tags 918, 920, or using other data characterization techniques.

Alternatively, for the operation 1306 (not shown), the graphical illustration may be provided based on the at least one dataset, the at least one dataset being associated with the at least one predictive basis through a characterization of the at least one dataset with respect to one or more of a source of the at least one dataset, a procedural aspect of the at least one dataset, a source of support associated with the at least one dataset, a research field of the at least one dataset, a time period or time interval of collection of the at least one dataset, a professional publication associated with the at least one dataset, a professional author or investigator associated with the at least one dataset, or a location of collection of the at least one dataset. For example, the at least one dataset may be characterized by a source or nature of the support of the research that supplied the results of the at least one dataset, where, for example, a certain nature of support may be associated with a higher net predictive value than others. Similarly, a research field associated with the at least one dataset (e.g., oncology or hematology) may be associated with, or characterized as, having a greater or lesser predictive value, e.g., through use of the tags 918, 920, or using other data characterization techniques.

Figure 14:
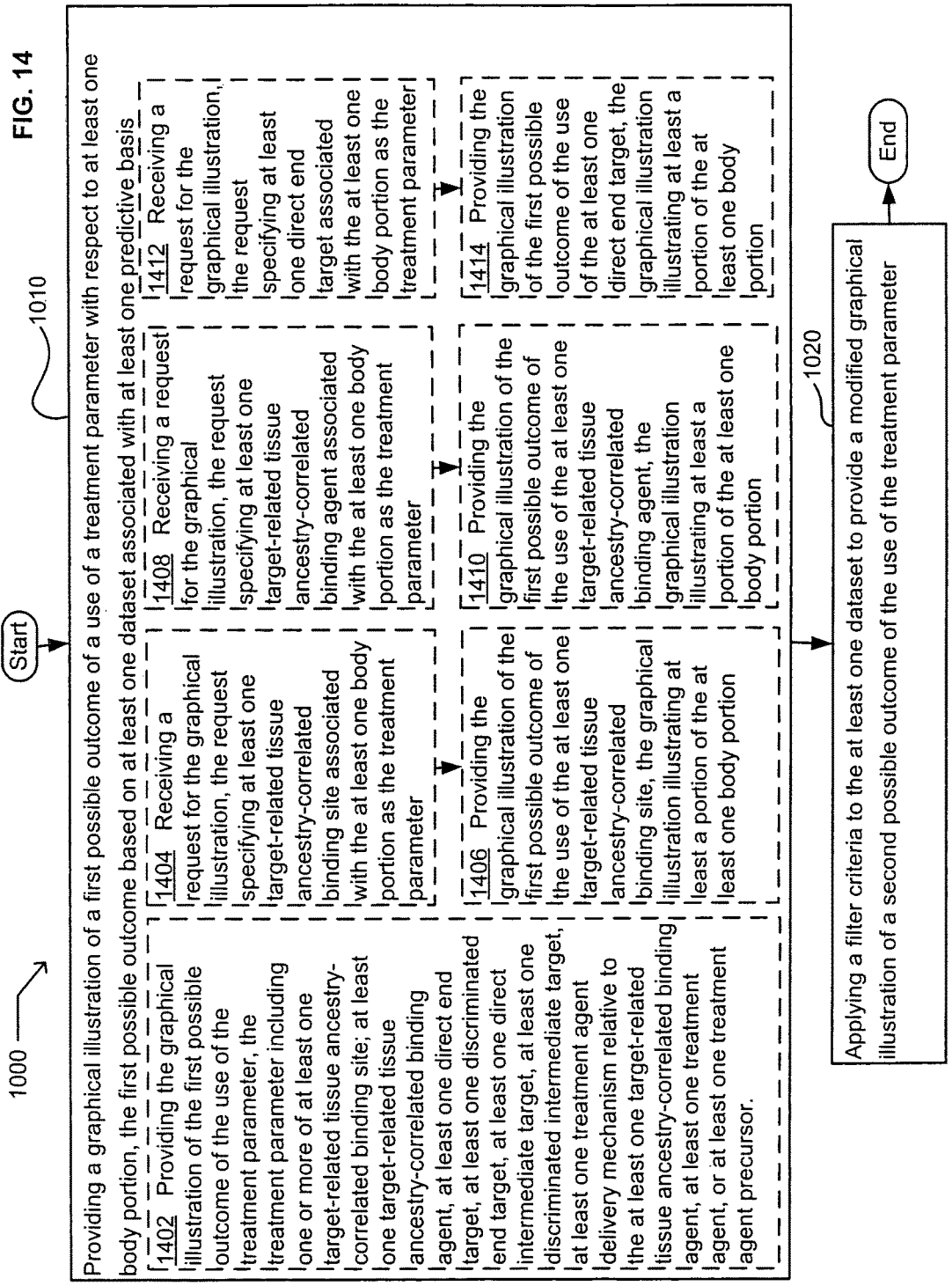
FIG. 14 illustrates an alternative embodiment of the example operational flow of FIG. 10.

FIG. 14 illustrates alternative embodiments of the example operational flow 1000 of FIG. 10. FIG. 14 illustrates example embodiments where the providing operation 1010 may include at least one additional operation. Additional operations may include operation 1402, operation 1404, operation 1406, operation 1408, operation 1410, operation 1412, and/or operation 1414.

At the operation 1402, the graphical illustration of the first possible outcome of the use of the treatment parameter may be provided, where the treatment parameter may include one or more of at least one target-related tissue ancestry-correlated binding site; at least one target-related tissue ancestry-correlated binding agent, at least one direct end target, at least one discriminated end target, at least one direct intermediate target, at least one discriminated intermediate target, at least one treatment agent delivery mechanism relative to the at least one target-related tissue ancestry-correlated binding agent, at least one treatment agent, or at least one treatment agent precursor. For example, the graphical illustration 802 may illustrate a first possible outcome of the use of one or more of a direct end target, a treatment agent, or a target-related tissue ancestry-correlated binding agent, as these or other examples of the operation 1402 may be selected, provided, or otherwise specified, using the fields 804-810, or similar fields.

At the operation 1404, a request for the graphical illustration may be received, the request specifying at least one target-related tissue ancestry-correlated binding site associated with the at least one body portion as the treatment parameter. For example, the user interface 132 may receive a request from the clinician 104 through the use of a field similar to the fields 804-810, or through another display element 902, wherein the clinician 104 specifies, for example, at least one protein induced and/or expressed at an interface (e.g., the endothelial layer 118) between tissue and/or blood and/or a blood component in the vicinity of the at least one body portion as the at least one target-related tissue ancestry-correlated binding site. Then, at the operation 1406, the graphical illustration of the first possible outcome of the use of the at least one target-related tissue ancestry-correlated binding site may be provided, the graphical illustration illustrating at least a portion of the at least one body portion. For example, the at least a portion of the at least one body portion (e.g., at least a portion of the lungs 108) may be illustrated in the graphical illustration 802 (e.g., including a visual indicator) as to an efficacy of the at least one target-related tissue ancestry-correlated binding site in serving as a molecular address for the treatment agent of the field 806.

At the operation 1408, a request for the graphical illustration may be received, the request specifying at least one target-related tissue ancestry-correlated binding agent associated with the at least one body portion as the treatment parameter. For example, the user interface 132 may receive a request for the at least one target-related tissue ancestry-correlated binding agent by way of the field(s) 808 and/or 810. The at least one target-related tissue ancestry-correlated binding agent may include, for example, an I-labeled monoclonal antibody that is known to target and bind to a corresponding target-related tissue ancestry-correlated binding site. Then, at the operation 1410, the graphical illustration of the first possible outcome of the use of the at least one target-related tissue ancestry-correlated binding agent may be provided, the graphical illustration illustrating at least a portion of the at least one body portion. For example, as in FIG. 8, if the target-related tissue ancestry-correlated binding agent is associated with a corresponding target-related tissue ancestry-correlated binding site of the lungs 108 (or certain cancerous cells thereof), then the lungs 108 may be illustrated in whole or in part.

At the operation 1412, a request for the graphical illustration may be received, the request specifying at least one direct end target associated with the at least one body portion as the treatment parameter. For example, the request for the graphical illustration 802 to include the (requested) direct end target may be specified using the field 804 of the user interface 132. Then, at the operation 1414, the graphical illustration of the first possible outcome of the use of the at least one direct end target may be provided, the graphical illustration illustrating at least a portion of the at least one body portion. For example, the graphical illustration 802 may be provided as showing the lungs 108 or the pancreas 110 as the at least one body portion (since, in the latter case, the lungs 108 are associated with the pancreas 110 by virtue of an (undesired) effect on the pancreas 110 that may be included in the first possible outcome).

Figure 15:
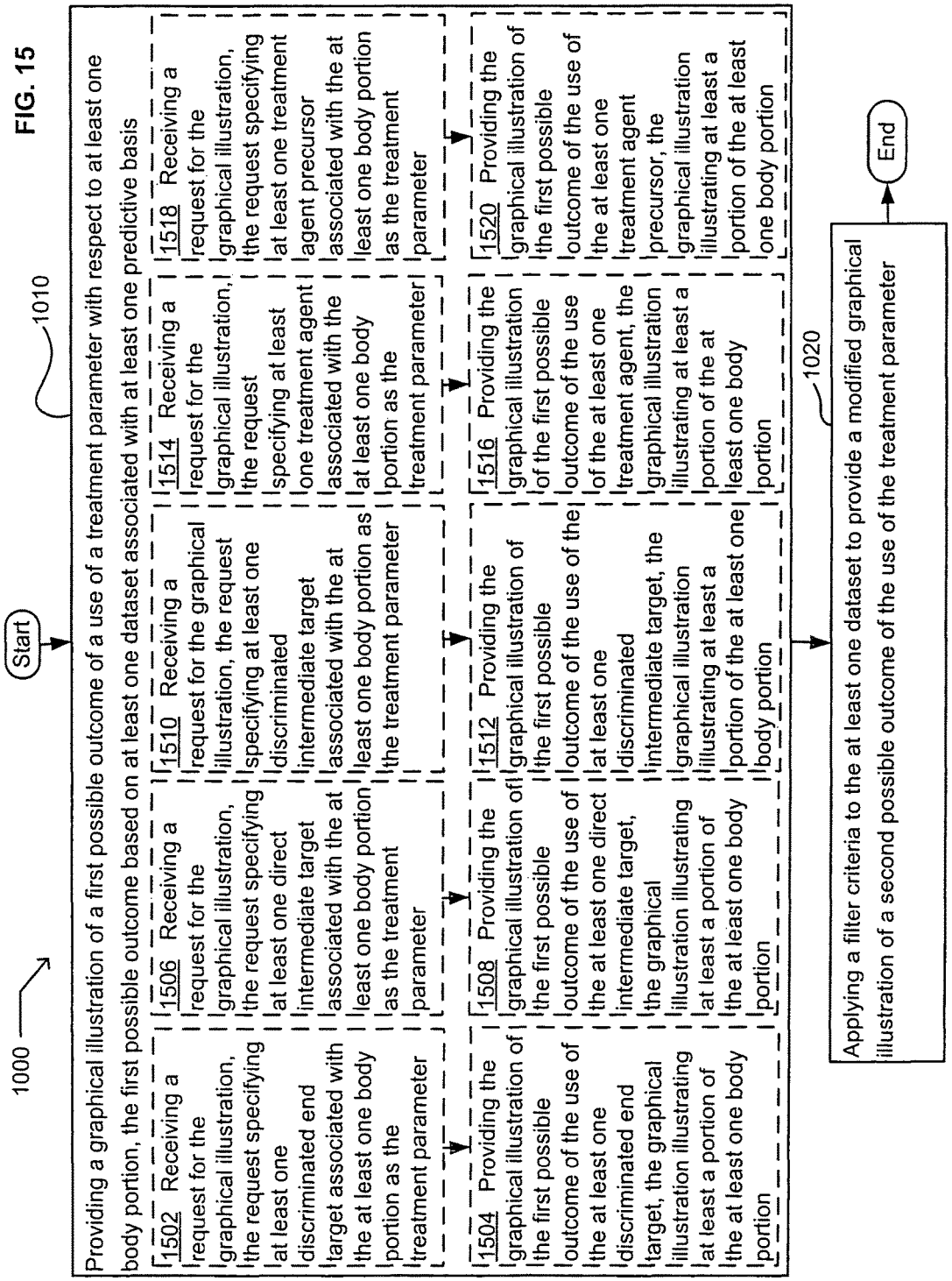
FIG. 15 illustrates an alternative embodiment of the example operational flow of FIG. 10.

FIG. 15 illustrates alternative embodiments of the example operational flow 1000 of FIG. 10. FIG. 15 illustrates example embodiments where the providing operation 1010 may include at least one additional operation. Additional operations may include operation 1502, operation 1504, operation 1506, operation 1508, operation 1510, operation 1512, operation 1514, operation 1516, operation 1518, and/or operation 1520.

At the operation 1502, a request for the graphical illustration is received, the request specifying at least one discriminated end target associated with the at least one body portion as the treatment parameter. For example, although not illustrated in FIG. 8, a corresponding field of the user interface 132 may be used to receive the request for the at least one discriminated end target. Then, at the operation 1504, the graphical illustration of the first possible outcome of the use of the at least one discriminated end target may be provided, the graphical illustration illustrating at least a portion of the at least one body portion. For example, the discriminated end target may include non-lung tissue/organ(s) (e.g., the pancreas 110), and/or non-cancerous lung tissue, so that one or more of these may be included in the graphical illustration 802.

At the operation 1506, a request for the graphical illustration may be received, the request specifying at least one direct intermediate target associated with the at least one body portion as the treatment parameter. For example, the direct intermediate target may be specified using a field (not shown) of FIG. 8. Then, at the operation 1508, the graphical illustration of the first possible outcome of the use of the at least one direct intermediate target may be provided, the graphical illustration illustrating at least a portion of the at least one body portion. For example, the direct intermediate target may include endothelial tissue proximate to (e.g., cancerous) lung tissue, so that the graphical illustration 802 may illustrate at least a portion of the lungs 108.

At the operation 1510, a request for the graphical illustration may be received, the request specifying at least one discriminated intermediate target associated with the at least one body portion as the treatment parameter. For example, the discriminated intermediate target may be specified using a field (not shown) of FIG. 8. Then, at the operation 1512, the graphical illustration of the first possible outcome of the use of the at least one discriminated intermediate target may be provided, the graphical illustration illustrating at least a portion of the at least one body portion. For example, the discriminated intermediate target may include endothelial tissue proximate to non-lung tissue (e.g., endothelial tissue proximate to the pancreas 110), so that the graphical illustration 802 may illustrate the lungs 108 and/or the pancreas 110 (or a portion thereof) as the at least a portion of the at least one body portion.

At the operation 1514, a request for the graphical illustration may be received, the request specifying at least one treatment agent associated with the at least one body portion as the treatment parameter. For example, the user interface 132 may receive the request by way of the field 806. Then, at the operation 1516, the graphical illustration of the first possible outcome of the use of the at least one treatment agent may be provided, the graphical illustration illustrating at least a portion of the at least one body portion. For example, where the treatment agent includes radionuclides that are associated with cancer cells in the lung through a desired course of treatment, then the graphical illustration 802 may provide an illustration of the lungs 108, perhaps with a visual indicator to indicate a presence of the treatment agent (e.g., radionuclides).

At the operation 1518, a request for the graphical illustration may be received, the request specifying at least one treatment agent precursor associated with the at least one body portion as the treatment parameter. For example, the treatment agent precursor may be specified using a field (not shown) of FIG. 8. Then, at the operation 1520, the graphical illustration of the first possible outcome of the use of the at least one treatment agent precursor may be provided, the graphical illustration illustrating at least a portion of the at least one body portion. For example, the treatment agent precursor may include an agent used to facilitate application of a treatment agent, e.g., an immune-response element that is used to identify/mark/bond with a target-related tissue ancestry-correlated binding site and/or a substance that when metabolized becomes the treatment agent, such as with pro-drugs.

Figure 16:
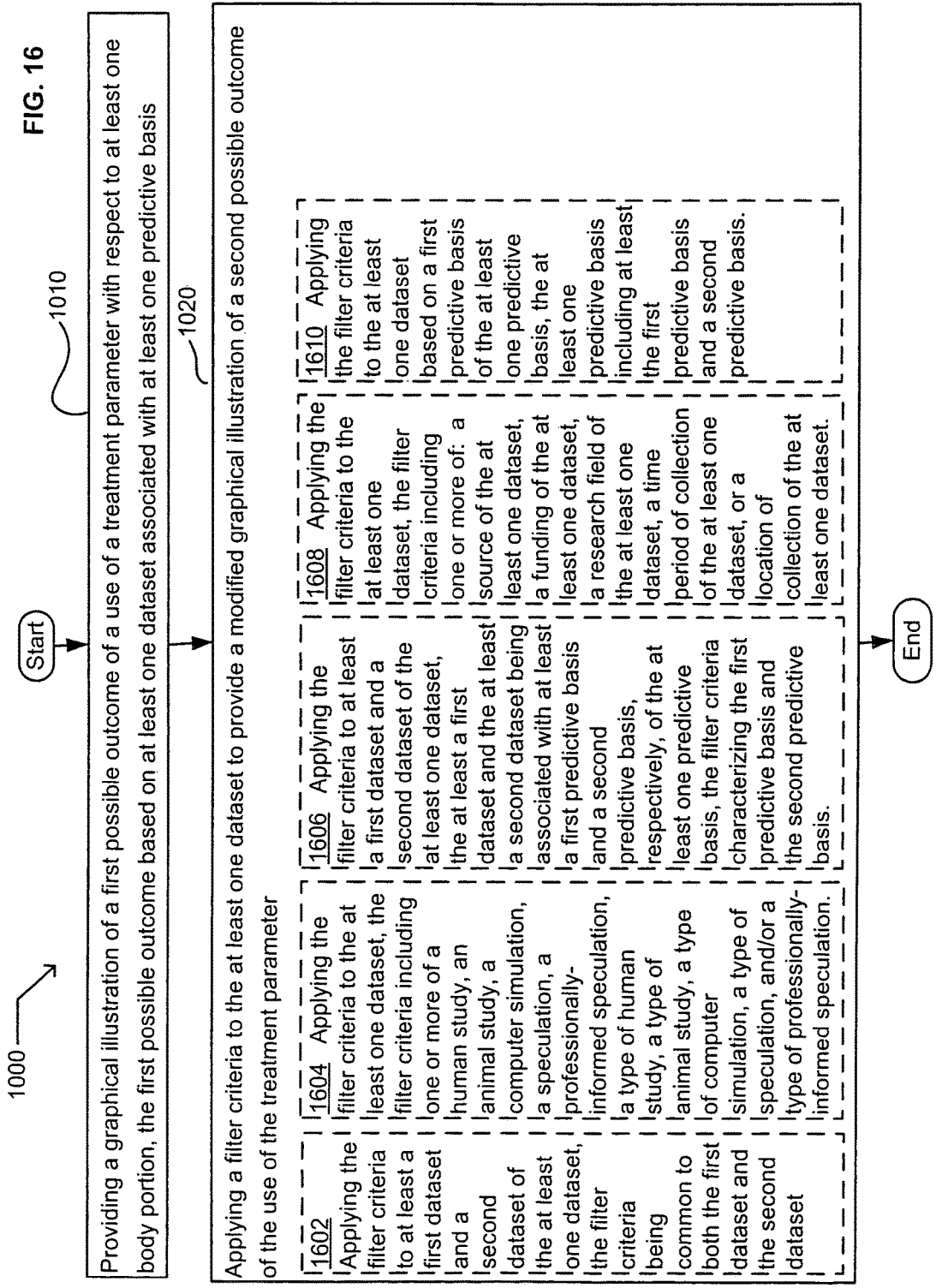
FIG. 16 illustrates an alternative embodiment of the example operational flow of FIG. 10.

FIG. 16 illustrates alternative embodiments of the example operational flow 1000 of FIG. 10. FIG. 16 illustrates example embodiments where the applying operation 1020 may include at least one additional operation. Additional operations may include operation 1602, operation 1604, operation 1606, operation 1608, and/or operation 1610.

At the operation 1602, the filter criteria may be applied to at least a first dataset and a second dataset of the at least one dataset, the filter criteria being common to both the first dataset and the second dataset. For example, the clinician 104 may select "human studies" and "animal studies" as the first dataset and the second dataset, respectively, using the field 812 of FIG. 8. Then, the clinician 104 may select a filter criteria such as "using protocol x," using the field 814, where, in this example, both the first dataset and the second dataset may include results that were obtained using "protocol x." In this way, applying the filter criteria may be seen to "cut across," or include/exclude results from, both the first dataset and the second dataset.

In one implementation, applying the filter criteria of the field 814 may be seen to remove all results obtained using "protocol x," while, in another implementation, applying the filter criteria of the field 814 may be seen to retain only the results using "protocol x." In other words, the filter criteria of the field 814 may be understood to represent either a negatively-phrased recitation of information to be removed, or a positive recitation of information to be retained. In some implementations, both filter options may be presented to the clinician 104, e.g., according to a preference of the clinician 104.

At the operation 1604, the filter criteria may be applied to the at least one dataset, the filter criteria including one or more of a human study, an animal study, a computer simulation, a speculation, a professionally-informed speculation, a type of human study, a type of animal study, a type of computer simulation, a type of speculation, and/or a type of professionally-informed speculation. For example, the field 814 may be used to select "animal studies" as a dataset to be applied as the filtering criteria, e.g., when a plurality of datasets (including the "animal studies" dataset) are selected using the field 812.

At the operation 1606, the filter criteria may be applied to at least a first dataset and a second dataset of the at least one dataset, the at least a first dataset and the at least a second dataset being associated with at least a first predictive basis and a second predictive basis, respectively, of the at least one predictive basis, the filter criteria characterizing the first predictive basis and the second predictive basis. For example, the clinician 104 may select "human studies" and "animal studies" as the first dataset and the second dataset, respectively, using the field 812 of FIG. 8, so that the graphical illustration 802 is provided based on data associated with these datasets. The filter criteria may characterize the first predictive basis and the second predictive basis as being either more or less predictively useful, as described herein, so that, for example, the clinician 104 may request filtering of results that are relatively less (or relatively more) predictive usefulness.

For example, a data manager/creator of the treatment data 126, which may include the clinician 104, may make such assignment or association between different predictive bases relative to one another. As described herein, for example, the second dataset associated with "animal studies" may be deemed to be less predictively useful than the first dataset associated with "human studies." In other examples, different types of "human studies" may be included/specified/requested, and may be pre-designated, e.g., using the tags 918, 920, to indicate an assigned level of predictive usefulness, based, for example, on a time, location, or protocol of the studies, or on a preference of the clinician 104, or on some other criteria. In this way, a burden on, or effort of, the clinician 104 may be reduced, while the clinician 104 is allowed, for example, to filter or reduce a query as to an efficacy of the treatment parameter by considering datasets being characterized as being relatively more predictively useful. For example, the graphical illustration 802 may be provided/modified to reflect the second possible outcome and the second predictive basis, with a color (or other visual indicator) of the relevant body portion(s) being altered accordingly.

At the operation 1608, the filter criteria may be applied to the at least one dataset, the filter criteria including one or more of: a source of the at least one dataset, a funding of the at least one dataset, a research field of the at least one dataset, a time period of collection of the at least one dataset, or a location of collection of the at least one dataset. For example, the clinician 104 may select "region x" as the filter criteria, using the field 814, the "region x" corresponding to a location of collection of the at least one dataset.

At the operation 1610, the filter criteria may be applied to the at least one dataset based on a first predictive basis of the at least one predictive basis, the at least one predictive basis including at least the first predictive basis and a second predictive basis. For example, the at least one dataset may include all available results, as may be selected using the "aggregation" option of the field 812, so that at least first and second predictive bases are used that may include "in silico" and/or "speculation." Then, the filter criteria of the field 814 may be applied to the aggregated dataset (results), based on, for example, the predictive basis of "speculation," so that, again for example, speculative results may be removed from the results upon which the modified graphical illustration showing the second possible outcome is based. It should be understood in this example, and from the description provided herein, that a given predictive basis, e.g., "speculation," may be associated with a plurality of individual datasets, so that filtering based on such a predictive basis may remove a plurality of individual datasets of results.

Figure 17:
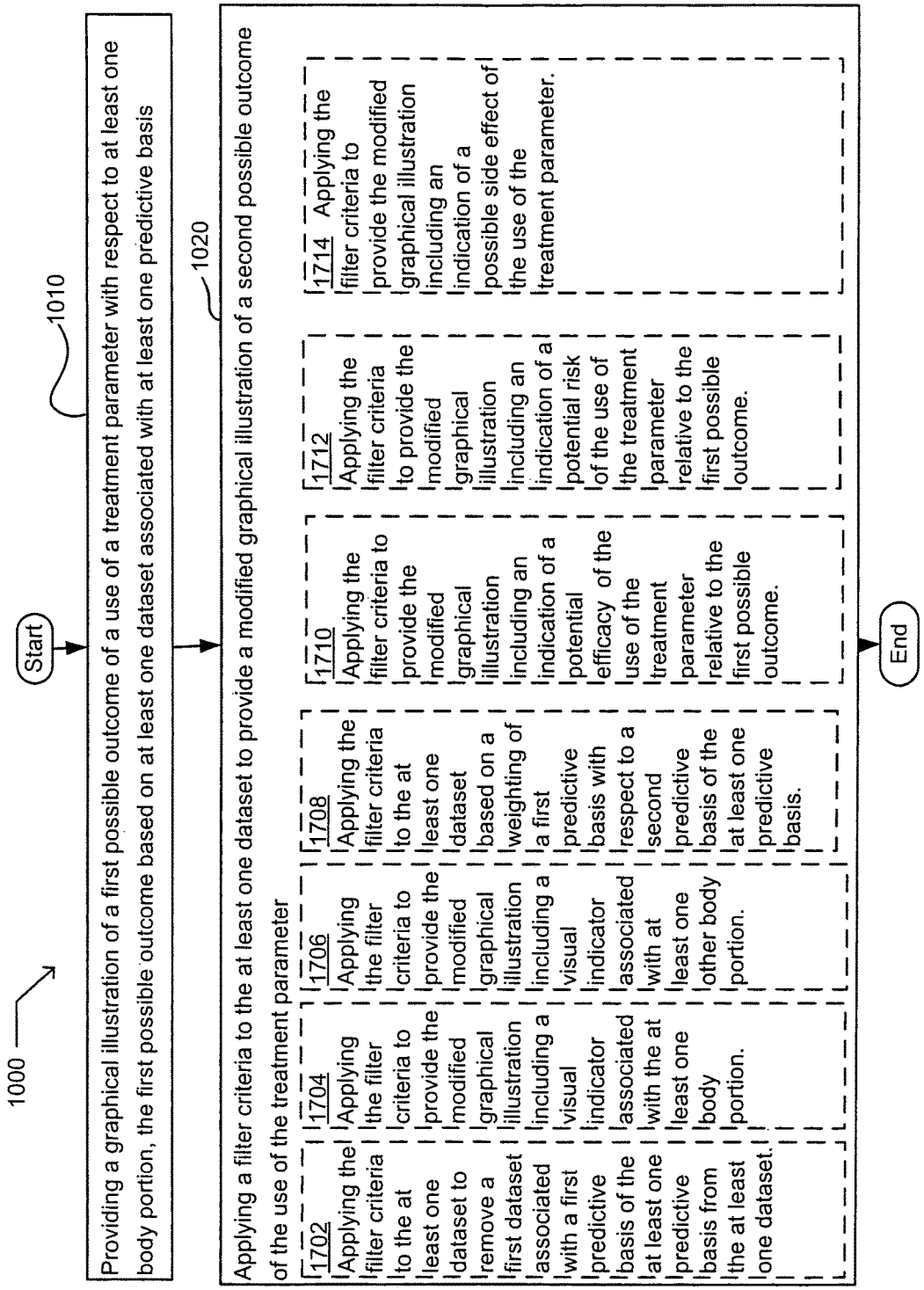
FIG. 17 illustrates an alternative embodiment of the example operational flow of FIG. 10.

FIG. 17 illustrates alternative embodiments of the example operational flow 1000 of FIG. 10. FIG. 17 illustrates example embodiments where the applying operation 1020 may include at least one additional operation. Additional operations may include operation 1702, operation 1704, operation 1706, operation 1708, operation 1710, operation 1712, and/or operation 1714.

At the operation 1702, the filter criteria may be applied to the at least one dataset to remove a first dataset associated with a first predictive basis of the at least one predictive basis from the at least one dataset. For example, as above, the at least one dataset may include all available results, as may be selected using the "aggregation" option of the field 812. Then, for example, a specified dataset associated with "human studies" may be removed from the aggregated results.

At the operation 1704, the filter criteria may be applied to provide the modified graphical illustration including a visual indicator associated with the at least one body portion. For example, a visual indicator associated with the at least one body portion may be modified within the modified graphical illustration. For example, where the at least one predictive basis supporting the first possible outcome includes "human studies" and "animal studies" selected from the field 812, the applying the filter criteria may remove results associated with "animal studies." Accordingly, the second possible outcome may be different than the first possible outcome in some respect. For example, the first possible outcome may show a high efficacy of the treatment agent in the field 806, and/or a relatively low incidence of impact of the treatment agent on undesired tissue (e.g., on the pancreas 110). Meanwhile, the second possible outcome may show, for example, an even higher efficacy of the treatment agent, combined with a relatively high degree of impact of the treatment agent on undesired tissue. Thus, in the operation 1602, a visual indicator associated with the lungs 108, such as, for example, a color, may be modified to indicate/illustrate such changes between the first possible outcome and the second possible outcome At the operation 1706, the filter criteria may be applied to provide the modified graphical illustration including a visual indicator associated with at least one other body portion. For example, a visual indicator associated with at least one other body portion within the graphical illustration 802 may be modified. For example, and continuing the example(s) just provided, a color or other visual indicator associated with at least one other body portion besides the lungs 108, e.g., the pancreas 110, may be modified in the second possible outcome, relative to the first possible outcome.

At the operation 1708, the filter criteria may be applied to the at least one dataset based on a weighting of a first predictive basis with respect to a second predictive basis of the at least one predictive basis. For example, considering a case where the at least one dataset includes datasets for "human studies" and "animal studies," the filter criteria may be applied based on a weighting of the two predictive bases relative to one another within the at least one dataset, e.g., to filter out heavily-weighted (or lightly-weighted) results for providing the second possible outcome.

At the operation 1710, the filter criteria may be applied to provide the modified graphical illustration including an indication of a potential efficacy of the use of the treatment parameter relative to the first possible outcome. For example, in applying the filer criteria, the graphical illustration 802 may be modified in visual appearance in any of the manners described herein, or in other manners not necessarily described, in order to illustrate the second possible outcome with respect to a potential efficacy of the use of the treatment parameter relative to the first possible outcome. For example, the lungs 108 may be visually modified within the modified graphical illustration, relative to a visual appearance of the lungs 108 in the graphical illustration 802 provided in association with the providing operation 1010.

At the operation 1712, the filter criteria may be applied to provide the modified graphical illustration including an indication of a potential risk (e.g., a traditional risk or an ambiguity) of the use of the treatment parameter relative to the first possible outcome. For example, the graphical illustration 802 may be modified in visual appearance in any of the manners described herein, or in other manners not necessarily described, in order to illustrate the second possible outcome with respect to a potential risk of the use of the treatment parameter relative to the first possible outcome.

At the operation 1714, the filter criteria may be applied to provide the modified graphical illustration including an indication of a possible side effect of the use of the treatment parameter. For example, the graphical illustration 802 may be modified to illustrate the second possible outcome with respect to a side effect of the use of the treatment parameter relative to the first possible outcome. For example, a side effect of the treatment agent of the field 806 on the pancreas 110 may be included in the second possible outcome based on the applying the filtering criteria, by altering a visual appearance of, or indicator associated with, the pancreas 110.

Figure 18:
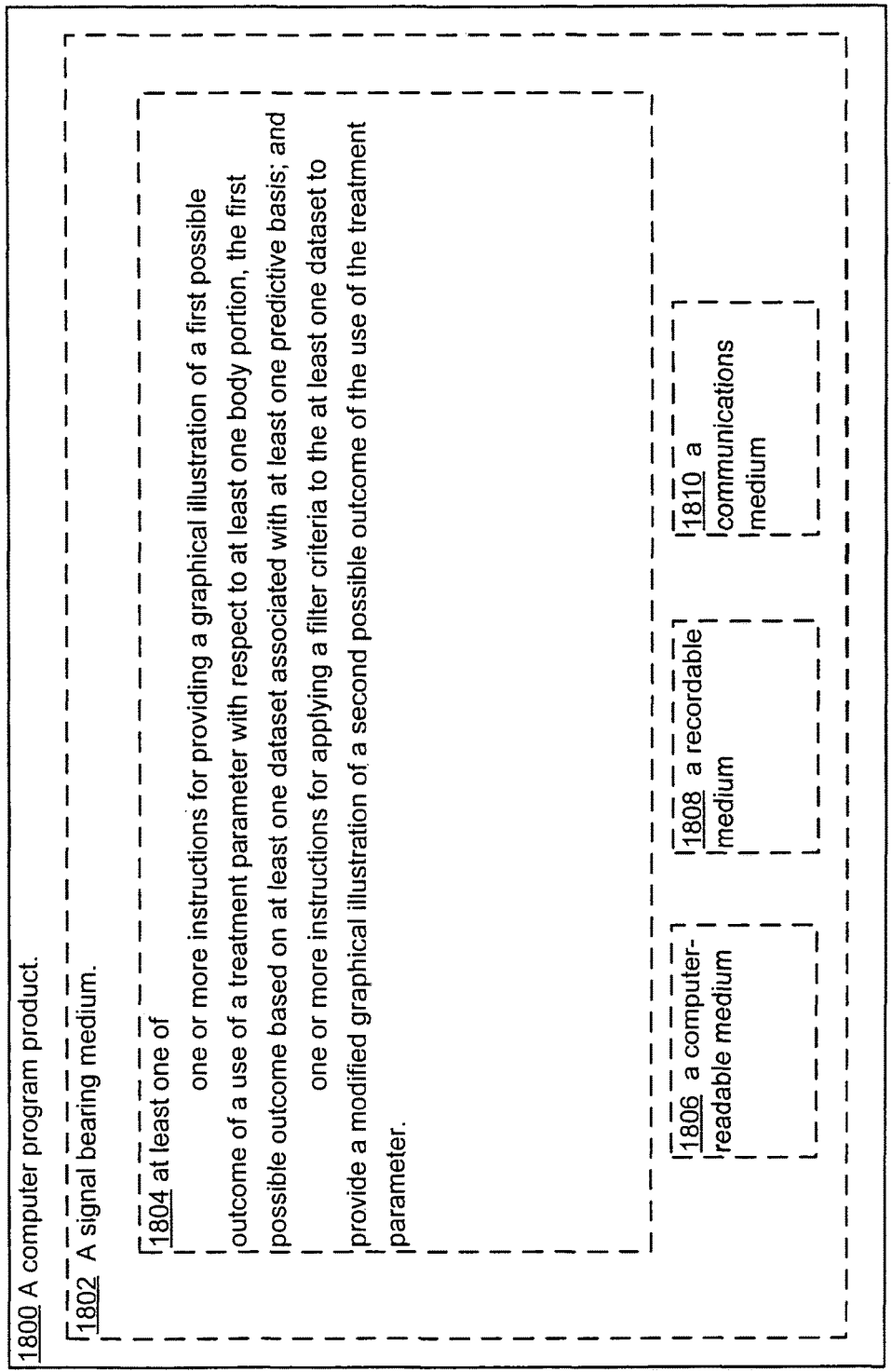
FIG. 18 illustrates a partial view of an example computer program product that includes a computer program for executing a computer process on a computing device.

FIG. 18 illustrates a partial view of an example computer program product 1800 that includes a computer program 1804 for executing a computer process on a computing device. An embodiment of the example computer program product 1800 is provided using a signal bearing medium 1802, and may include at least one of one or more instructions for providing a graphical illustration of a first possible outcome of a use of a treatment parameter with respect to at least one body portion, based on a first dataset associated with a first predictive basis, and one or more instructions for modifying the graphical illustration to illustrate a second possible outcome of the use of the treatment parameter, based on a second dataset associated with a second predictive basis. The one or more instructions may be, for example, computer executable and/or logic-implemented instructions. In one implementation, the signal-bearing medium 1802 may include a computer-readable medium 1806. In one implementation, the signal bearing medium 1802 may include a recordable medium 1808. In one implementation, the signal bearing medium 1802 may include a communications medium 1810.

Figure 19:
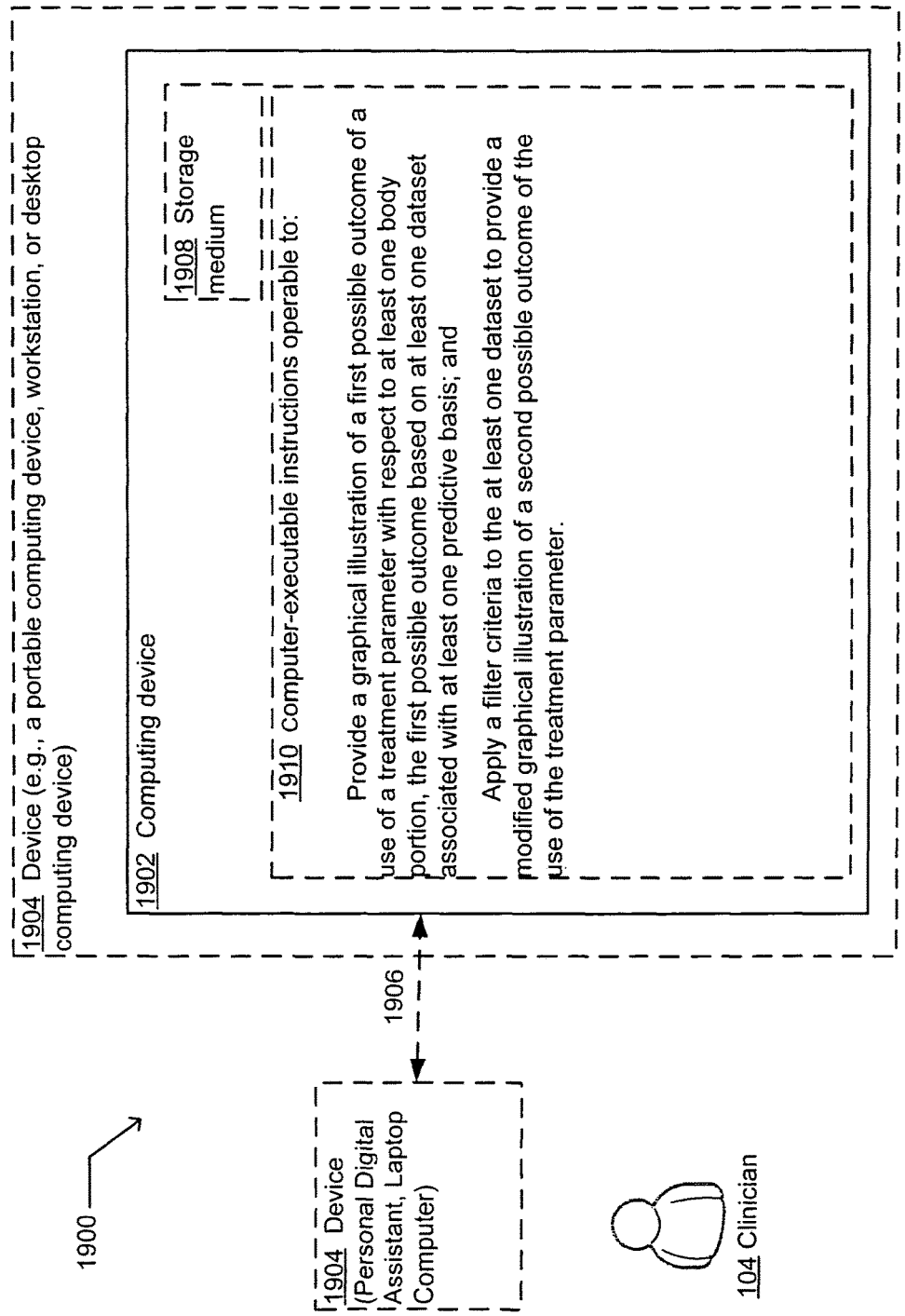
FIG. 19 illustrates an example device in which embodiments may be implemented.

FIG. 19 illustrates an example system 1900 in which embodiments may be implemented. The system 1900 includes a computing system environment. The system 1900 also illustrates the clinician 104 using a device 1904, which is optionally shown as being in communication with a computing device 1902 by way of an optional coupling 1906. The optional coupling 1906 may represent a local, wide-area, or peer-to-peer network, or may represent a bus that is internal to a computing device (e.g., in example embodiments in which the computing device 1902 is contained in whole or in part within the device 1904). A storage medium 1908 may be any computer storage media.

The computing device 1902 includes computer-executable instructions 1910 that when executed on the computing device 1902 cause the computing device 1902 to provide a graphical illustration of a first possible outcome of a use of a treatment parameter with respect to at least one body portion, based on a first dataset associated with a first predictive basis, and to modify the graphical illustration to illustrate a second possible outcome of the use of the treatment parameter, based on a second dataset associated with a second predictive basis. As referenced above and as shown in FIG. 19, in some examples, the computing device 1902 may optionally be contained in whole or in part within the clinician device 1904.

In FIG. 19, then, the system 1900 includes at least one computing device (e.g., 1902 and/or 1904). The computer-executable instructions 1910 may be executed on one or more of the at least one computing device. For example, the computing device 1902 may implement the computer-executable instructions 1910 and output a result to (and/or receive data from) the computing (clinician) device 1904. Since the computing device 1902 may be wholly or partially contained within the computing (clinician) device 1904, the computing (clinician) device 1904 also may be said to execute some or all of the computer-executable instructions 1910, in order to be caused to perform or implement, for example, various ones of the techniques described herein, or other techniques.

The clinician device 1904 may include, for example, one or more of a personal digital assistant (PDA), a laptop computer, a tablet personal computer, a networked computer, a computing system comprised of a cluster of processors, a workstation computer, and/or a desktop computer. In another example embodiment, the computing device 1902 may be operable to communicate with the clinician device 1904 associated with the clinician 104 to receive information regarding the identification and to provide the at least two instances of the at least one treatment characteristic from at least one memory.

In addition to references described above, the following are also hereby incorporated by reference in their entireties to the extent such are not inconsistent herewith:

Pasqualini et al., "Probing the Structural and Molecular Diversity of Tumor Vasculature," TRENDS in Molecular Medicine, vol. 8, No. 12, pp. 563-571 (December 2002);

Aird et al., "Vascular Bed-specific Expression of an Endothelial Cell Gene is Programmed by the Tissue Microenvironment," The Journal of Cell Biology, vol. 138, No. 5, pp. 1117-1124 (Sep. 8, 1997);

Pasqualini et al., "Organ Targeting In Vivo Using Phage Display Peptide Libraries," Nature, vol. 380, pp. 364-366 (Mar. 28, 1996);

Rajotte et al., "Molecular Heterogeneity of the Vascular Endothelium Revealed by In Vivo Phage Display," J. Clin. Invest., vol. 102, No. 2, pp. 430-437 (July 1998);

M'Rini, et al., "A Novel Endothelial L-Selectin Ligand Activity in Lymph Node Medulla That Is Regulated by (1,3)-Fucosyltransferase-IV," J. Exp. Med., vol. 198, No. 9, pp. 1301-1312 (Nov. 3, 2003);

Carver, et al., "Caveolae: Mining Little Caves for New Cancer Targets," Nature Reviews, vol. 3, pp. 571-572 (August 2003);

Folkman, Judah, "Looking For A Good Endothelial Address," Cancer Cell, pp. 113-115 (March 2002);

Brody, Lawrence C., "Treating Cancer by Targeting a Weakness," N Engl J Med, 353; 9 pp. 949-950 (1 Sep. 2005);

Farmer, et al., "Targeting the DNA Repair Defect in BRCA Mutant Cells as a Therapeutic Strategy," Nature, vol. 434, pp. 917-921 (14 Apr. 2005);

Bryant, et al., "Specific Killing of BRCA2-Deficient Tumours with Inhibitors of poly(ADP-ribose) Polymerase," Nature, vol. 434, pp. 913-917 (14 Apr. 2005).

Hsu, et al., "Neural Systems Responding to Degrees of Uncertainty in Human Decision-Making," Science, vol. 310, 1680-1683 (9 Dec. 2005).

Kaplan, et al., "VEGFR1-Postive Haematopoietic Bone Marrow Progenitors Initiate The Pre-Metastatic Niche," Nature, vol. 438, pp. 820-825 (8 Dec. 2005).

Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermediate components. Likewise, any two components so associated can also be viewed as being "operably connected," or "operably coupled," to each other to achieve the desired functionality. Any two components capable of being so associated can also be viewed as being "operably couplable" to each other to achieve the desired functionality. Specific examples of operably couplable include but are not limited to physically mateable and/or physically interacting components and/or wirelessly interactable and/or wirelessly interacting components and/or logically interacting and/or logically interactable components.

While certain features of the described implementations have been illustrated as disclosed herein, many modifications, substitutions, changes and equivalents will now occur to those skilled in the art. It is, therefore, to be understood that the appended claims are intended to cover all such modifications and changes as fall within the true spirit of the embodiments of the invention.

While particular aspects of the present subject matter described herein have been shown and described, it will be apparent to those skilled in the art that, based upon the teachings herein, changes and modifications may be made without departing from this subject matter described herein and its broader aspects and, therefore, the appended claims are to encompass within their scope all such changes and modifications as are within the true spirit and scope of this subject matter described herein. Furthermore, it is to be understood that the invention is solely defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

What is claimed is:

1. A system comprising:
   circuitry configured for receiving at least one genetic characteristic representative of at least one patient associated with at least one treatment parameter;
   circuitry configured for receiving input identifying at least one direct end target associated with the at least one treatment parameter, the at least one direct end target including at least one target-related tissue ancestry-correlated binding site;
   circuitry configured for providing a first possible treatment agent, the first possible treatment agent based at least partly on at least one first predictive basis associated with the at least one treatment parameter and the at least one direct end target;
   circuitry configured for applying a filter criteria based at least partly on at least one second predictive basis associated with the received at least one genetic characteristic, the at least one second predictive basis indicative of a second possible treatment agent; and
   circuitry configured for determining whether one of the first possible treatment agent or the second possible treatment agent is a preferred treatment agent for the at least one patient based at least partly on the received at least one genetic characteristic.

2. The system of claim 1, wherein the circuitry configured for providing a first possible treatment agent, the first possible treatment agent based at least partly on at least one first predictive basis associated with the at least one treatment parameter and the at least one direct end target comprises:
   circuitry configured for providing a graphical illustration of at least part of a body that visually indicates a first possible outcome of a use of a treatment agent with respect to efficacy of the treatment agent, the first possible outcome based at least partly on the at least one first predictive basis.

3. The system of claim 1, wherein the circuitry configured for identifying at least one direct end target associated with at least one treatment parameter comprises:
   circuitry configured for identifying at least one direct intermediate target associated with the at least one treatment parameter.

4. The system of claim 1, wherein the circuitry configured for providing a first possible treatment agent, the first possible treatment agent based at least partly on at least one first predictive basis associated with the at least one treatment parameter and the at least one direct end target comprises:
   circuitry configured for providing a graphical illustration, the graphical illustration including the at least one discriminated intermediate target associated with at least one body portion.

5. The system of claim 1, wherein the circuitry configured for providing a first possible treatment agent comprises:
   circuitry configured for identifying at least one treatment agent associated with at least one of the at least one direct end target or the at least one treatment parameter.

6. The system of claim 1, wherein the circuitry configured for receiving input identifying at least one direct end target associated with the at least one treatment parameter comprises:
   circuitry configured for identifying at least one treatment agent precursor associated with at least one of the at least one direct end target or the at least one treatment parameter.

7. The system of claim 1, wherein the circuitry configured for providing a first possible treatment agent, the first possible treatment agent based at least partly on at least one first predictive basis associated with the at least one treatment parameter and the at least one direct end target comprises:
   circuitry configured for providing an indication of efficacy associated with the first possible treatment agent, the indication of efficacy at least partly based on the received at least one genetic characteristic.

8. The system of claim 1, wherein the circuitry configured for providing a first possible treatment agent, the first possible treatment agent based at least partly on at least one first predictive basis associated with the at least one treatment parameter and the at least one direct end target comprises:
   circuitry configured for providing a graphical illustration of at least part of the body that visually indicates a potential risk associated with the first possible outcome of the use of the treatment agent.

9. The system of claim 1, wherein the circuitry configured for applying a filter criteria based at least partly on at least one second predictive basis associated with the received at least one genetic characteristic, the at least one second predictive basis indicative of a second possible treatment agent comprises:
   circuitry configured for applying at least one of the following types of filter criteria to provide a second possible treatment agent: human study, animal study, computer simulation, date, region, or protocol.

10. The system of claim 1, wherein the circuitry configured for providing a first possible treatment agent, the first possible treatment agent based at least partly on at least one first predictive basis associated with the at least one treatment parameter and the at least one direct end target comprises:
circuitry configured for providing a first possible outcome of a use of a treatment agent with respect to one or more of the following: organ, organ system, organ subsystem, diseased tissue, and healthy tissue.

11. The system of claim 1, wherein the circuitry configured for providing a first possible treatment agent, the first possible treatment agent based at least partly on at least one first predictive basis associated with the at least one treatment parameter and the at least one direct end target comprises:
circuitry configured for providing a first systemic consequence of a use of a treatment agent based at least partly on the at least one first predictive basis associated with the at least one treatment parameter and based at least partly on the received at least one genetic characteristic.

12. The system of claim 1, wherein the circuitry configured for providing a first possible treatment agent, the first possible treatment agent based at least partly on at least one first predictive basis associated with the at least one treatment parameter and the at least one direct end target comprises:
circuitry configured for providing a first possible outcome of a use of at least one of the following types of treatment agents: medication, imaging, and radio-immunotherapy.

13. The system of claim 1, wherein the circuitry configured for receiving input identifying at least one direct end target associated with the at least one treatment parameter, the at least one direct end target including at least one target-related tissue ancestry-correlated binding site comprises:
circuitry configured for deriving at least one three-dimensional representation of a particular patient based on data received from one or more image sensors, and
wherein the circuitry configured for providing a first possible treatment agent, the first possible treatment agent based at least partly on at least one first predictive basis associated with the at least one treatment parameter and the at least one direct end target includes at least:
circuitry configured for providing a graphical indication associated with the at least one three-dimensional representation of the individual regarding a first possible outcome of a use of a treatment agent, the first possible outcome based at least partly on the at least one first predictive basis.

14. The system of claim 1, wherein the circuitry configured for providing a first possible treatment agent, the first possible treatment agent based at least partly on at least one first predictive basis associated with the at least one treatment parameter and the at least one direct end target comprises:
circuitry configured for providing a first possible treatment agent based at least partly on an indication that the at least one directed target is diseased, and
wherein the circuitry configured for applying a filter criteria based at least partly on at least one second predictive basis associated with the received at least one genetic characteristic, the at least one second predictive basis indicative of a second possible treatment agent includes at least
circuitry configured for applying a filter criteria based at least partly on at least one indication that the first possible treatment agent is contraindicated for the at least one patient, the at least one indication based at least partly on the received at least one genetic characteristic.

15. The system of claim 1, further comprising:
circuitry configured for identifying at least one discriminated end target associated with the at least one treatment parameter based at least partly on at least one indication that the at least one treatment parameter is associated with a high risk of negative impact on the at least one discriminated end target.

16. The system of claim 1, wherein the circuitry configured for receiving input identifying at least one direct end target associated with the at least one treatment parameter comprises:
circuitry configured for identifying at least one treatment parameter associated with at least one end target based at least partly on at least one indication that at least one portion of the end target is diseased, and
wherein the circuitry configured for applying a filter criteria based at least partly on at least one second predictive basis associated with the received at least one genetic characteristic, the at least one second predictive basis indicative of a second possible treatment agent includes at least:
circuitry configured for determining that at least one portion of the end target is non-diseased based at least partly on the received at least one genetic characteristic
circuitry configured for providing at least one probabilistic outcome associated with application of the treatment parameter to the direct end target;
circuitry configured for providing at least one probabilistic outcome associated with at least one side effect of the at least one treatment parameter associated with the at least one portion of the end target that is non-diseased; and
circuitry configured for providing at least one probabilistic outcome associated with application of the treatment parameter to the portion of the end target that is non-diseased.

17. The system of claim 1, wherein the circuitry configured for receiving input identifying at least one direct end target associated with the at least one treatment parameter, the at least one direct end target including at least one target-related tissue ancestry-correlated binding site comprises:
circuitry configured for identifying at least one target-related tissue ancestry-correlated binding agent associated with a preferred treatment based at least partly on the at least one treatment parameter; and
circuitry configured for identifying body portions containing at least one target-related tissue ancestry-correlated binding site associated with the at least one target-related tissue ancestry-correlated binding agent.

18. The system of claim 1, further comprising:
circuitry configured for determining whether at least one discriminated end target associated with the at least one treatment parameter includes the at least one target-related tissue ancestry-correlated binding site associated with the at least one direct end target, and
wherein the circuitry configured for determining whether one of the first possible treatment agent or the second possible treatment agent is a preferred treatment agent for the at least one patient based at least partly on the received at least one genetic characteristic includes at least:

circuitry configured for determining an alternative treatment agent based on the determination whether the at least one discriminated end target associated with the at least one treatment parameter includes the at least one target-related tissue ancestry-correlated binding site associated with the at least one direct end target.

19. The system of claim 1, wherein the circuitry configured for receiving at least one genetic characteristic representative of at least one patient associated with at least one treatment parameter comprises:
circuitry configured for receiving at least one genetic characteristic representative of the at least one patient associated with the at least one treatment parameter via at least one touch-input enabled graphical user interface.

20. The system of claim 1, wherein the circuitry configured for receiving input identifying at least one direct end target associated with the at least one treatment parameter comprises:
circuitry configured for highlighting at least one body portion on at least one touch-enabled visual display, the highlighting including the at least one direct end target at least partly based on the received input identifying the at least one direct end target.

21. The system of claim 1, wherein the circuitry configured for receiving input identifying at least one direct end target associated with the at least one treatment parameter comprises:
circuitry configured for highlighting at least one body portion on at least one touch-enabled visual display, the highlighting including at least one discriminated end target at least partly based on received input identifying at least one discriminated end target.

22. The system of claim 1, wherein the circuitry configured for receiving at least one genetic characteristic representative of at least one patient associated with at least one treatment parameter comprises:
circuitry configured for setting the at least one genetic characteristic as a primary key in a set of relational tables.

23. The system of claim 22, wherein the circuitry configured for applying a filter criteria based at least partly on at least one second predictive basis associated with the received at least one genetic characteristic, the at least one second predictive basis indicative of a second possible treatment agent comprises:
circuitry configured for identifying at least one foreign key within one or more relational tables including one or more treatment agents, the at least one foreign key corresponding to the primary key; and
circuitry configured for eliminating from consideration as a possible treatment agent any record that does not include the at least one foreign key.

24. A method for determining probable outcomes of treatments, comprising:
receiving at least one genetic characteristic representative of at least one patient associated with at least one treatment parameter;
receiving input identifying at least one direct end target associated with the at least one treatment parameter, the at least one direct end target including at least one target-related tissue ancestry-correlated binding site;
providing a first possible treatment agent, the first possible treatment agent based at least partly on at least one first predictive basis associated with the at least one treatment parameter and the at least one direct end target;
applying a filter criteria based at least partly on at least one second predictive basis associated with the received at least one genetic characteristic, the at least one second predictive basis indicative of a second possible treatment agent; and
determining whether one of the first possible treatment agent or the second possible treatment agent is a preferred treatment agent for the at least one patient based at least partly on the received at least one genetic characteristic.

25. A computer program product comprising:
a non-transitory signal-bearing medium bearing one or more instructions that, when executed by at least one computer, configure the at least one computer to perform operations including at least:
receive at least one genetic characteristic representative of at least one patient associated with at least one treatment parameter;
receive input identifying at least one direct end target associated with the at least one treatment parameter, the at least one direct end target including at least one target-related tissue ancestry-correlated binding site;
provide a first possible treatment agent, the first possible treatment agent based at least partly on at least one first predictive basis associated with the at least one treatment parameter and the at least one direct end target;
apply a filter criteria based at least partly on at least one second predictive basis associated with the received at least one genetic characteristic, the at least one second predictive basis indicative of a second possible treatment agent; and
determine whether one of the first possible treatment agent or the second possible treatment agent is a preferred treatment agent for the at least one patient based at least partly on the received at least one genetic characteristic.

* * * * *